(12) United States Patent
Stoddart et al.

(10) Patent No.: US 10,259,913 B2
(45) Date of Patent: Apr. 16, 2019

(54) VIOLOGEN-BASED ROTAXANES

(71) Applicants: Northwestern University, Evanston, IL (US); King Abdulaziz City for Science and Technology (KACST), Riyadh (SA)

(72) Inventors: James Fraser Stoddart, Evanston, IL (US); Yuping Wang, Chicago, IL (US); Marco Frasconi, Narni (IT); Junling Sun, Evanston, IL (US)

(73) Assignees: Northwestern University, Evanston, IL (US); King Abdulaziz City for Science and Technology (KACST), Riyadh (SA)

( * ) Notice: Subject to any disclaimer, the term of this patent is extended or adjusted under 35 U.S.C. 154(b) by 0 days.

(21) Appl. No.: 15/419,030

(22) Filed: Jan. 30, 2017

(65) Prior Publication Data

US 2017/0218135 A1 Aug. 3, 2017

Related U.S. Application Data

(60) Provisional application No. 62/288,701, filed on Jan. 29, 2016.

(51) Int. Cl.
C07D 213/57 (2006.01)
C08G 77/50 (2006.01)
C08G 83/00 (2006.01)

(52) U.S. Cl.
CPC ......... *C08G 83/007* (2013.01); *C07D 213/57* (2013.01)

(58) Field of Classification Search
None
See application file for complete search history.

(56) References Cited

U.S. PATENT DOCUMENTS

| 8,299,276 B2 | 10/2012 | Clark |
| 2011/0137025 A1* | 6/2011 | Yaghi ................ B01J 20/226 540/145 |
| 2015/0191470 A1 | 7/2015 | Fahrenbach et al. |

FOREIGN PATENT DOCUMENTS

WO    2003101955    12/2003

OTHER PUBLICATIONS

High Yield Synthesis of Polyrotaxane Constructed from Pillar[5]arene and Viologen Polymer and Stabilization of its Radical Cation, Ogoshi et al., Macromolecules 2010, 43, 7068-7072 (Year: 2010).*
Aida, T. et al. Functional supramolecular polymers. Science 2012, 335, 813-817.
Balzani, V. et al. Light powered molecular machines. Chem. Soc. Rev. 2009, 38, 1542-1550.
Barat, R. et al. A mechanically interlocked molecular system programmed for the delivery of an anticancer drug. Chem. Sci. 2015, 6, 2608-2613.

(Continued)

*Primary Examiner* — Peter A Salamon
(74) *Attorney, Agent, or Firm* — Ardus Intellectual Property Law, LLP

(57) ABSTRACT

Disclosed herein are nanoactuating rotaxanes comprising a threading component, the threading component comprising a oligoviologen, and at least two macrocylic components, wherein the oligoviologen is threaded through each of the macrocylic components. Also disclosed are methods for making and using the rotaxanes.

19 Claims, 25 Drawing Sheets

(56) References Cited

OTHER PUBLICATIONS

Barnes, J. C. et al. A Radically configurable six-state compound. Science 2013, 339, 429-433.
Bin Imran, A. et al. Extremely stretchable thermosensitive hydrogels by introducing slide-ring polyrotaxane cross-linkers and ionic groups into the polymer network. Nat. Commun. 2014, 5.
Bruns, C. J.; Stoddart, J. F. The mechanical bond: a work of art. Top. Curr. Chem. 2012, 323, 19-72.
Bruns, C. J.; Stoddart, J. F. Mechanically interlaced and interlocked donor-acceptor foldamers. Adv. Polym. Sci. 2013, 261,271-294.
Bruns, C. J.; Stoddart, J. F. Rotaxane-based molecular muscles. Acc. Chem. Res. 2014, 47, 2186-2199.
Cheng, C. Y. et al. An artificial molecular pump. Nat. Nanotechnol. 2015, 10, 547-553.
Coskun, A. et al. Great expectations: can artificial molecular machines deliver on their promise? Chem. Soc. Rev. 2012, 41, 19-30.
Coskun, A. et al. High hopes: can molecular electronics realise its potential? Chem. Soc. Rev. 2012, 41, 4827-4859.
Dawson, R. E. et al. The foundation of a light driven molecular muscle based on stilbene and alpha-cyclodextrin. Chem. Commun. 2008, 34, 3980-3982.
Du, G. Y. et al. Muscle-like supramolecular polymers: integrated motion from thousands of molecular machines. Angew. Chem. Int. Ed. 2012, 51, 12504-12508.
Durot, S. et al. Transition-metal-complexed catenanes and rotaxanes: from dynamic systems to functional molecular machines. Top. Curr. Chem. 2014, 354, 35-70.
Evans, N. H.; Beer, P. D. Advances in anion supramolecular chemistry: from recognition to chemical applications. Angew. Chem. Int. Ed. 2014, 53, 11716-11754.
Fahrenbach, A. C. et al. Radically enhanced molecular switches. J. Am. Chem. Soc. 2012, 134, 16275-16288.
Fahrenbach, A. C. et al. Solution-phase mechanistic study and solid-state structure of a tris(bipyridinium radical cation) inclusion complex. J. Am. Chem. Soc. 2012, 134, 3061-3072.
Feringa, B. L. Molecular machines springing into action. Nat. Chem. 2010, 2, 429-430.
Flood, A. H. et al. Whence molecular electronics? Science 2004, 306, 2055-2056.
Fulmer, G. R. et al. NMR chemical shifts of trace impurities: common laboratory solvents, organics, and gases in deuterated solvents relevant to the organometallic chemist. Organometallics 2010, 29, 2176-2179.
Gan, Q. A. et al. Helix-rod host-guest complexes with shuttling rates much faster than disassembly. Science 2011, 331, 1172-1175.
Gotz, G. et al. pi-Conjugated [2]catenanes based on oligothiophenes and phenanthrolines: efficient synthesis and electronic properties. Chem.—Eur. J. 2015, 21, 7193-7210.
Guichard, G.; Huc, I. Synthetic foldamers. Chem. Commun. 2011, 47, 5933-5941.
Hill, D. J. et al. A field guide to foldamers. Chem. Rev. 2001, 101, 3893-4011.
Inutsuka, M. et al. Highly dielectric and flexible polyrotaxane elastomer by introduction of cyano groups. Polymer 2015, 59, 10-15.
Katsuno, C. et al. Pressure-responsive polymer membranes of slide-ring gels with movable cross-links. Adv. Mater. 2013, 25, 4636-4640.
Kay, E. R. et al. Synthetic molecular motors and mechanical machines. Angew. Chem. Int. Ed. 2007, 46, 72-191.
Li, H. et al. Mechanical bond-induced radical stabilization. J. Am. Chem. Soc. 2013, 135, 456-467.
Luo, Z. et al. Engineering a hollow nanocontainer platform with multifunctional molecular machines for tumor-targeted therapy in vitro and in vivo. ACS Nano 2013, 7, 10271-10284.
Mattia, E.; Otto, S. Supramolecular systems chemistry. Nat. Nanotechnol. 2015, 10, 111-119.
Pinson, M. B. et al. Mobile rings on a polyrotaxane lead to a yield force. Macromolecules 2013, 46, 4191-4197.
Schneider, H. J. Dispersive interactions in solution complexes. Acc. Chem. Res. 2015, 48, 1815-1822.
Sessler, J. L.; Jayawickramarajah, J. Functionalized base-pairs: versatile scaffolds for self-assembly. Chem. Commun. 2005, 1939-1949.
Sharrett, Z. et al. The effect of boronic acid acidity on performance of viologen-based boronic acids in a two-component optical glucose-sensing system. Tetrahedron Lett 2007, 48, 5125-5129.
Takashima, Y. et al. Expansion-contraction of photoresponsive artificial muscle regulated by host-guest interactions. Nat. Commun. 2012, 3, 1270-1277.
Trabolsi, A. et al. Radically enhanced molecular recognition. Nat. Chem. 2010, 2, 42-49.
Van Quaethem, A. et al. Probing the mobility of catenane rings in single molecules. Chem. Sci. 2014, 5, 1449-1452.
Venturi, M.; Credi, A. Electroactive [2]catenanes. Electrochim. Acta 2014, 140, 467-475.
Wang, Y. et al. Folding of oligoviologens induced by radical-radical interactions. J. Am. Chem. Soc. 2015, 137, 876-885.
Wozny, M. et al. An electrochemically switchable foldamer—a surprising feature of a rotaxane with equivalent stations. Chem. Sci. 2014, 5, 2836-2842.
Zhang, D. W. et al. Aromatic amide and hydrazide foldamer-based responsive host-guest systems. Acc. Chem. Res. 2014, 47, 1961-1970.
Zhang, K. D. et al. Foldamer-tuned switching kinetics and meta-stability of [2]rotaxanes. Angew. Chem. Int. Ed. 2011, 50, 9866-9870.
Zhu, Z. et al. Synthesis and solution-state dynamics of donor-acceptor oligorotaxane foldamers. Chem. Sci. 2013, 4, 1470-1483.
Meng, Z. et al. Tristable [n]Rotaxanes: From Molecular Shuttle to Molecular Cable Car. Chem. Sci. 2013, 5, 1520-1525.
Witus, L.S. et al., Relative contractile motion of the rings in a switchable palindromic [p]rotaxane in aqueous solution driven by radical-pairing interactions. Organic Biomolecular Chem, 2014, 12, 6089-6093.
Zhang, W. et al., A solid-state switch containing an electrochemically switchable bistable poly[n]rotaxane, J Materials Chem, 2010, 21, 1487-1495.

\* cited by examiner

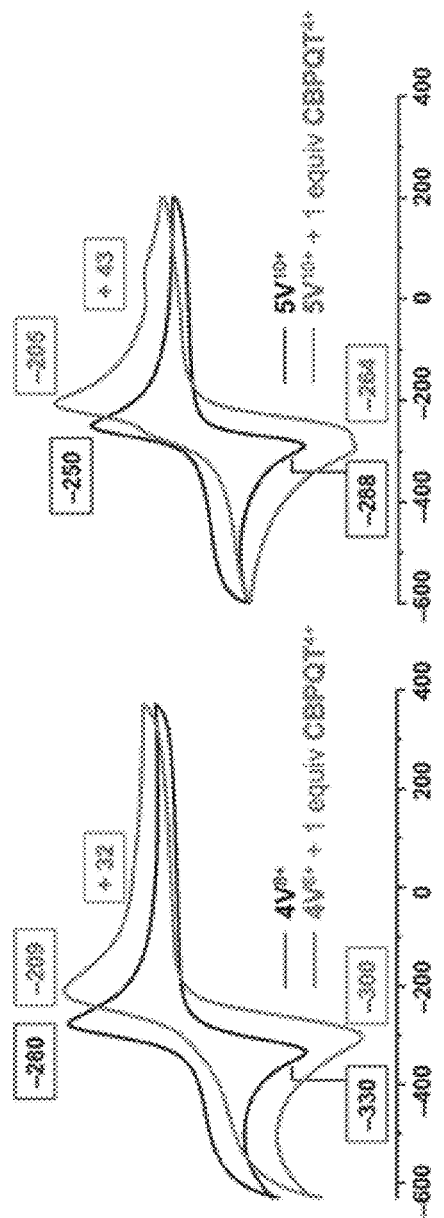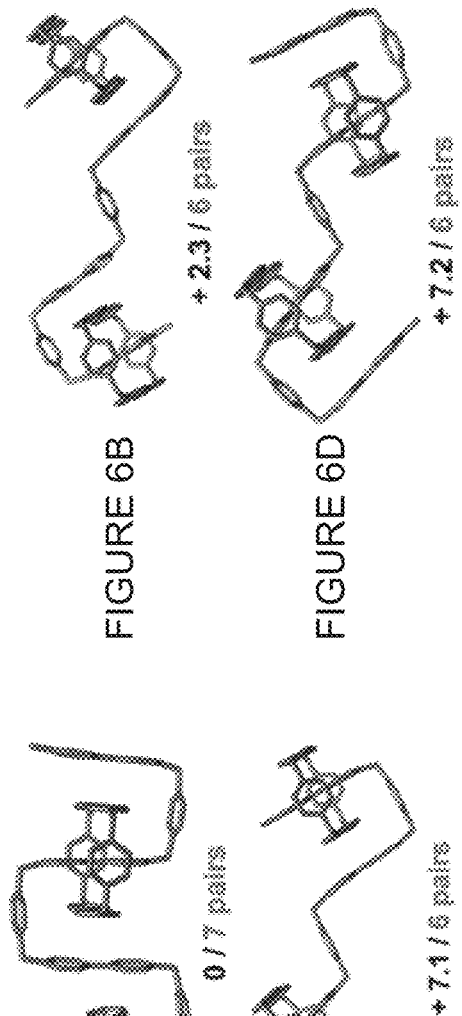
FIGURE 5A
FIGURE 5B
FIGURE 6A
FIGURE 6B
FIGURE 6C
FIGURE 6D

0 / 8 pairs

+ 10.0 / 7 pairs

+ 14.1 / 7 pairs

+ 20.2 / 6 pairs

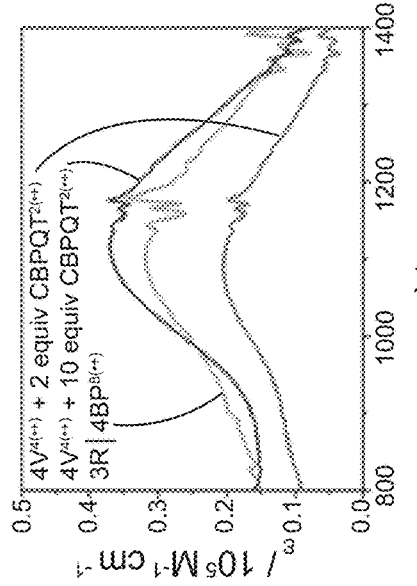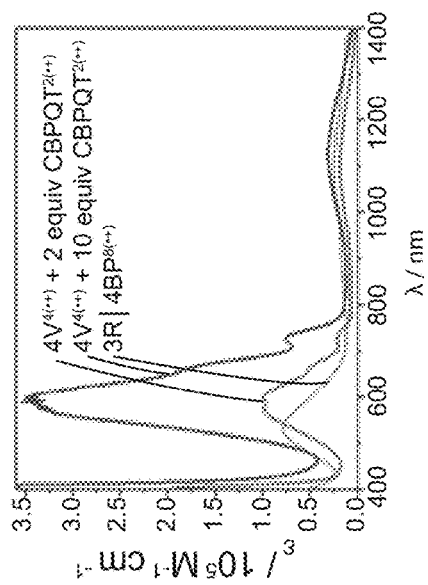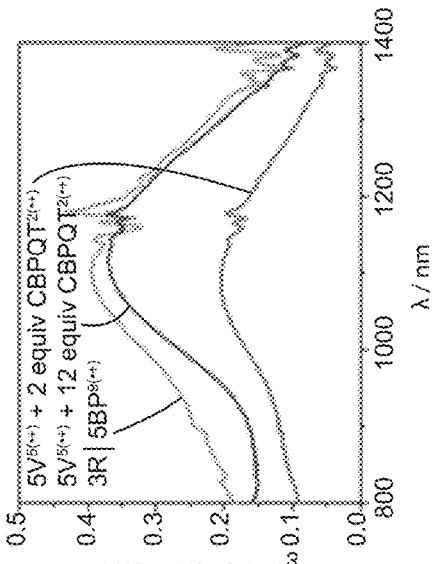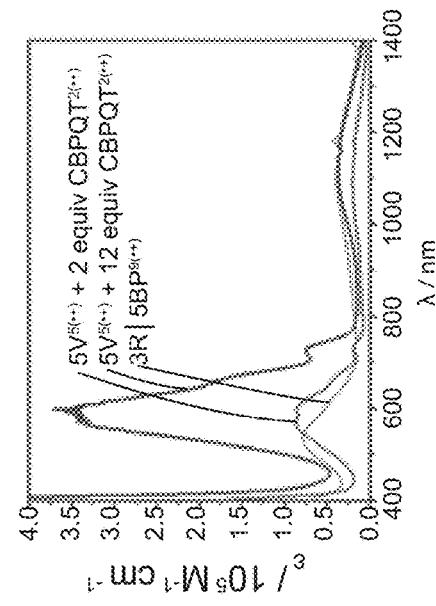
FIGURE 9A
FIGURE 9B
FIGURE 9C
FIGURE 9D

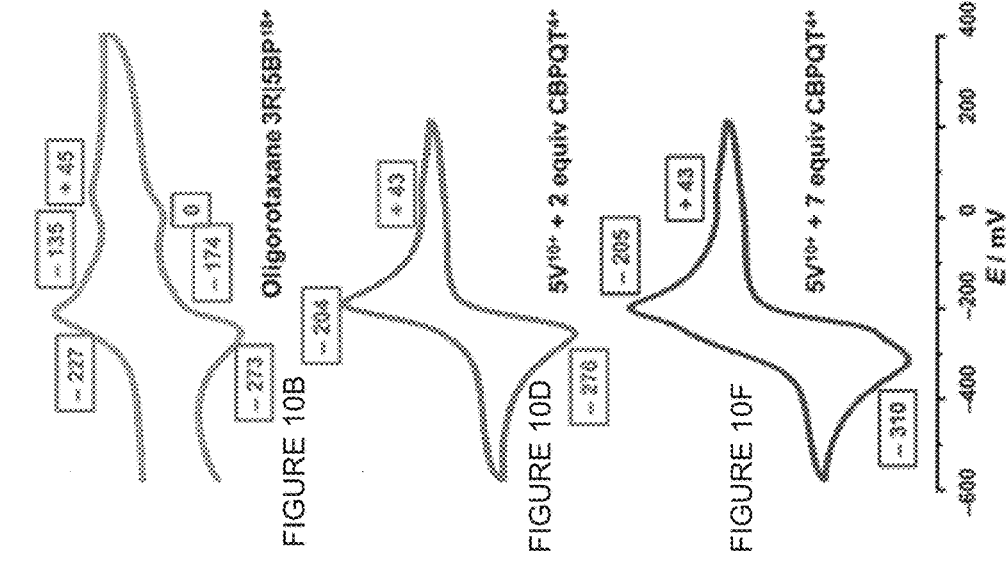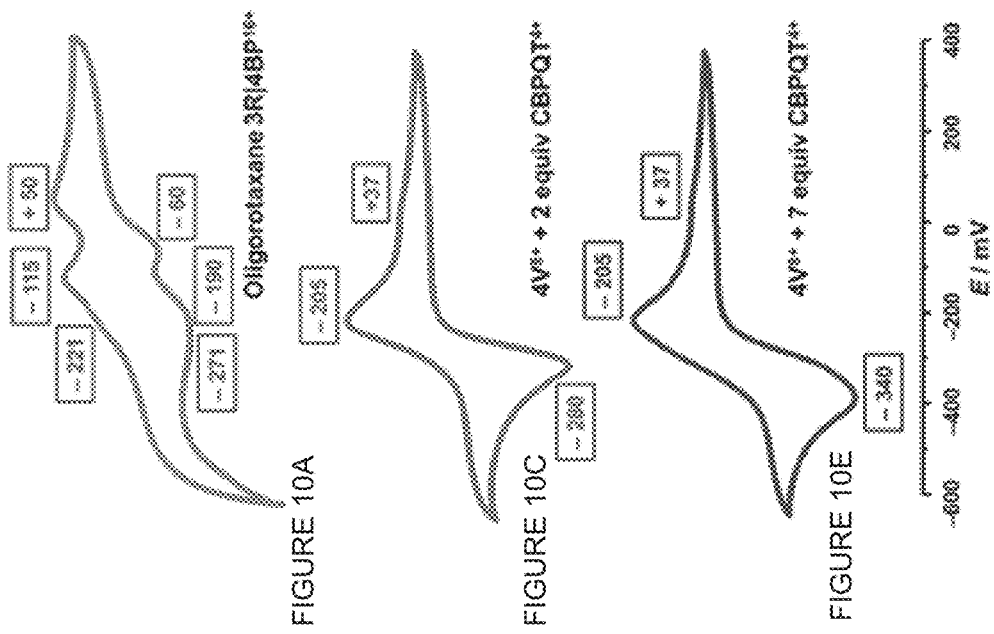

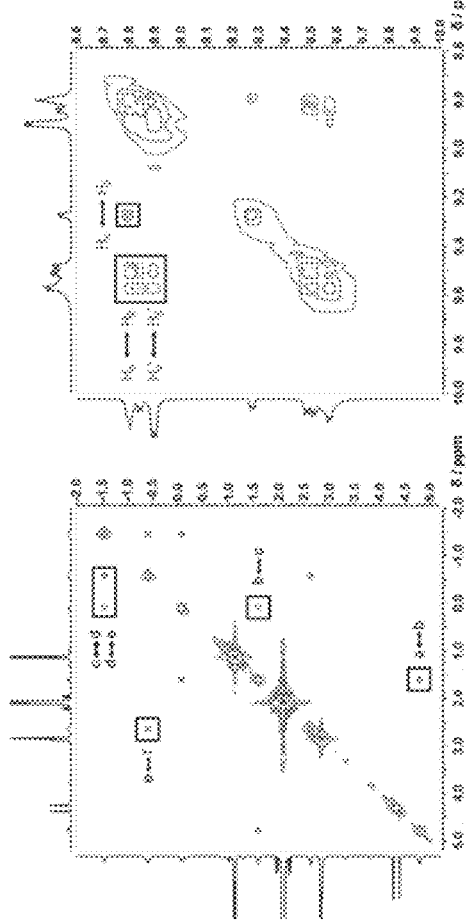
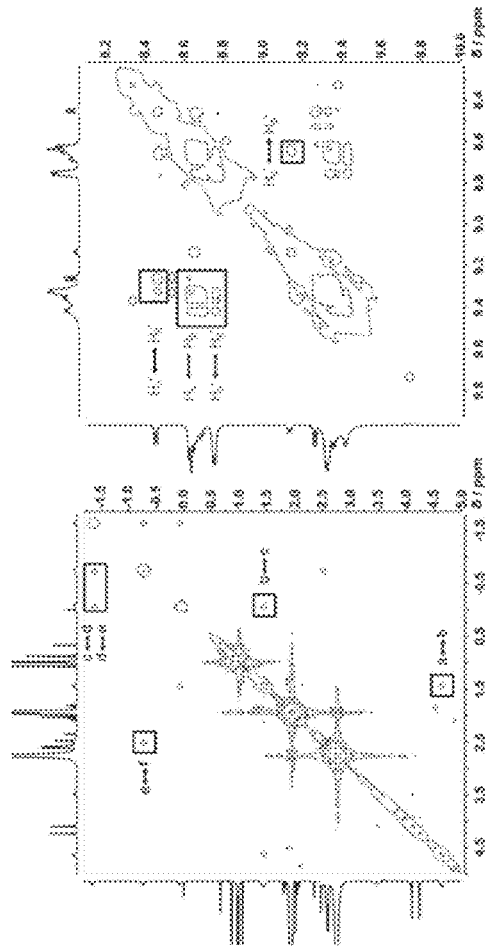
FIGURE 17A
FIGURE 17B
FIGURE 19A
FIGURE 19B

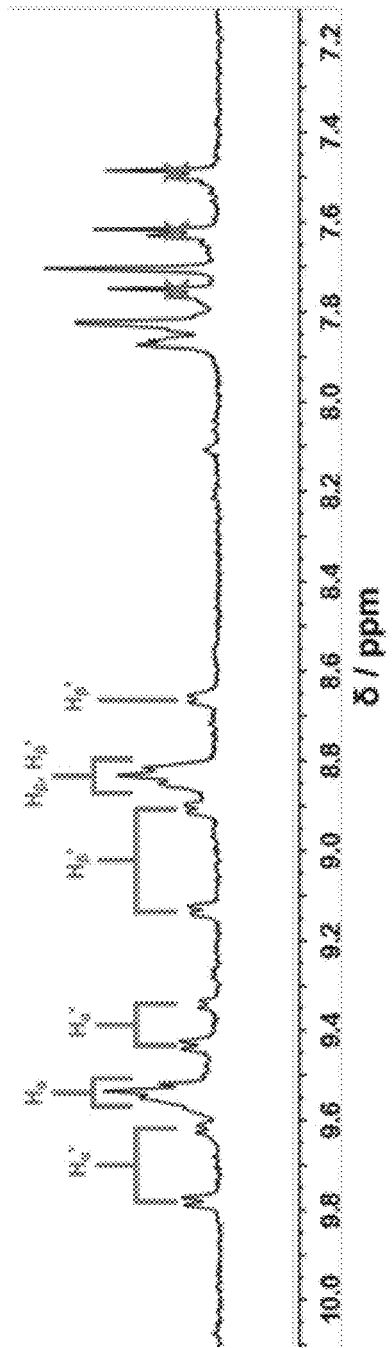
FIGURE 20
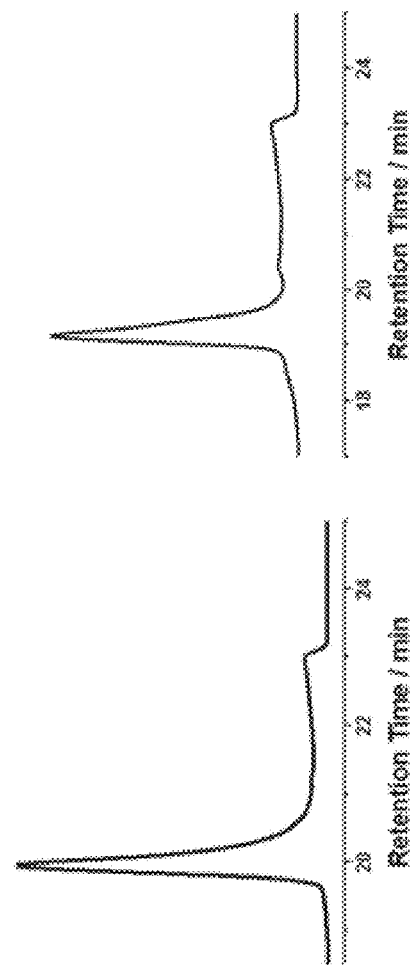
FIGURE 21A
FIGURE 21B

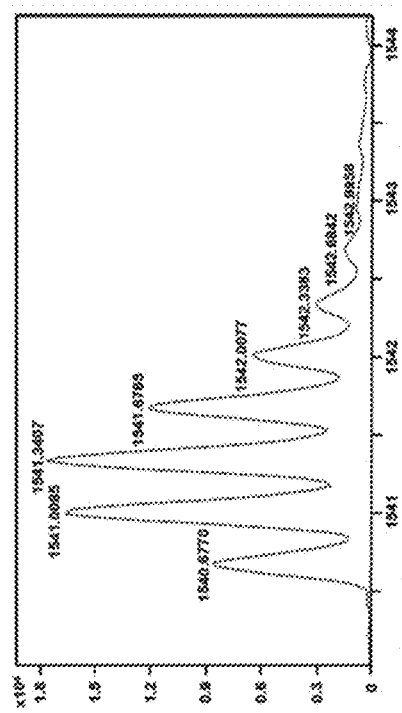
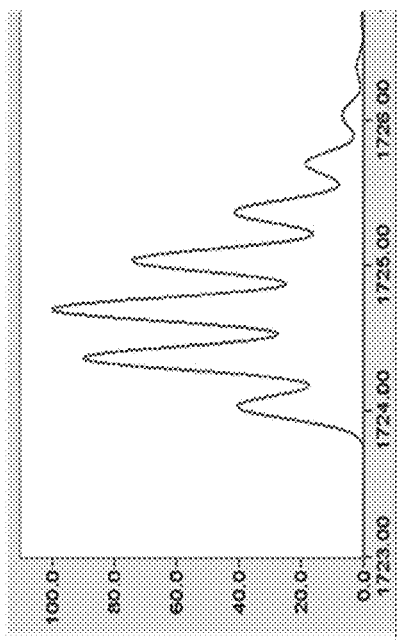
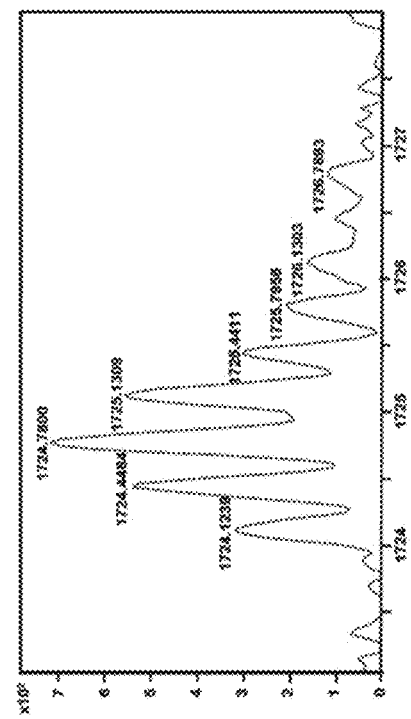
FIGURE 22A
FIGURE 22B
FIGURE 22C
FIGURE 22D

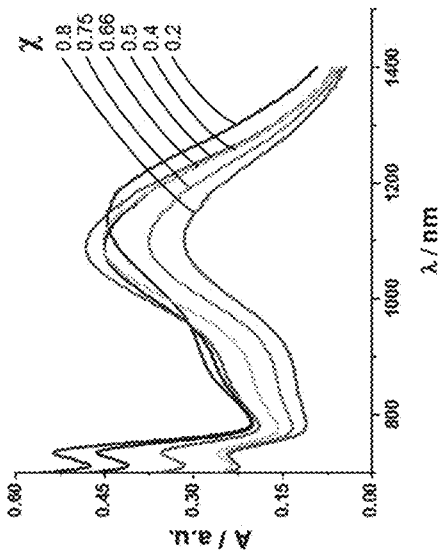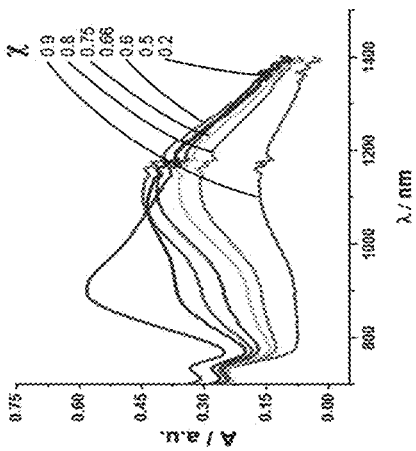
FIGURE 23A
FIGURE 23B
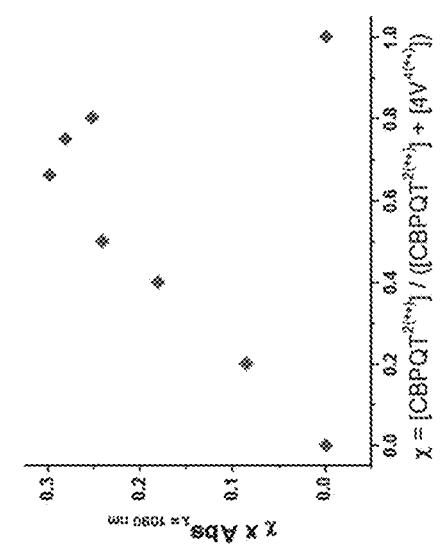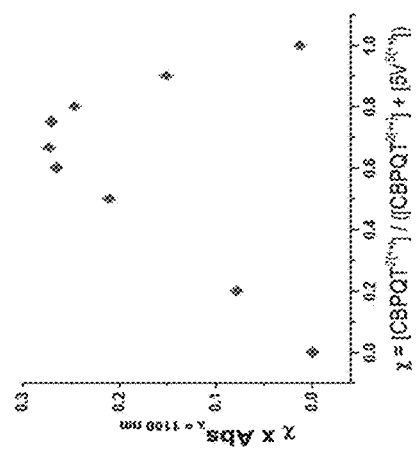
FIGURE 24A
FIGURE 24B

VIOLOGEN-BASED ROTAXANES

FIELD OF INVENTION

The disclosed technology is generally related to rotaxanes. More specifically, the disclosed technology is related to viologen-based rotaxanes.

BACKGROUND

Motivated by the desire to understand the structure-property relationships of biomolecules including DNA, RNA and membranes and the roles they play in life processes, chemists have striven to manipulate molecular-scale phenomena, resulting from noncovalent bonding interactions, in ever-increasingly complex and organized situations. [1-4] By employing noncovalent bonding interactions, synthetic foldamers,[5-8] which are promising candidates for mimicking the behavior of biomacromolecules under different kinds of stimuli—and mechanical interlocked molecules [9-11] (MIMs), which are the result of the formation of mechanical bonds and have already found applications in drug delivery[12, 13] and molecular electronics[14-17]—have been developed and investigated in some detail. Foldamers and MIMs, both utilizing intra- and intermolecular interactions in order to regulate the shapes of molecules, however, seldom result in their paths' crossing.

Foldameric rotaxanes,[18-21] which lie at the intersection between synthetic foldamers and MIMs, have made their ways into chemists' sights recently. Usually expressed in the context of oligorotaxanes, in which the dumbbell component is threaded by multiple ring components in order to regulate the folded secondary structure, they can exhibit remarkable physicochemical properties[22-26] in response to external stimuli. For example, it has already been[22, 23, 25] demonstrated that mechanical responses of oligorotaxanes toward external forces can be controlled by the mobile rings trapped along their one-dimensional dumbbell components, representing a new class of entropy-dominated molecules and materials.

To date, syntheses and properties of a family of foldameric oligorotaxanes which rely on the presence of donor-acceptor recognition between electron-rich 1,5-dioxanaphthalene (DNP) units and electron-deficient cyclobis (paraquat-p-phenylene) (CBPQT$^{4+}$) rings have been disclosed.[28] Moreover radical-pairing interactions associated with BIPY$^{(\cdot+)}$ radical cations—the mono reduced state of dicationic BIPY$^{2+}$ units—can be utilized in the preparation of MIMs based on a template-directing strategy.[29-33]

Foldameric oligorotaxanes make it possible to prepare functional materials by scaling[11,27] the concerted mechanical actuation of MIMs into the macroscopic regime where applications can be sought and witnessed. For the development of new applications and novel molecular devices and materials, there is a need for new rotaxanes that can be used to prepare nanoactuators.

SUMMARY OF THE INVENTION

Disclosed herein are viologen-based rotaxanes to prepare nanoactuators. In some embodiments, the nanoaccuator comprises a rotaxane, wherein the rotaxane comprises a threading component and at least two macrocylic components; wherein the threading component comprises a oligoviologen; and wherein the threading component is threaded through each of the macrocylic components. In another embodiment, the nanoaccuator comprises a rotaxane, wherein the rotaxane comprises a threading component; wherein the threading component comprising a linear subchain having a formula L-V—[B—V]$_n$-L', and at least two macrocycle components; wherein each of the at least two macrocycle components are threaded onto the threading component; and wherein V is a viologen subunit, B is a bridging subunit; wherein L and L' are linking subunits, and wherein n is an integer. The nanoactuator may further comprise a first stopper subunit, S, and a second stopper subunit, S', and wherein the threading component has a formula of S-L-V—[B—V]$_n$-L'-S'. In some embodiments, the at least two macrocylic components are CBPQT macrocylic components.

In some embodiments, the oligoviologen comprises a viologen subunit. The viologen subunits may be BIPY subunits. The oligoviolgen may further comprise bridging subunits linking the viologen subunits. The bridging subunit may be a paraxylene subunit. In particular embodiments, the oligoviologen comprises four or five viologen subunits.

The nanoactuator may further comprise a first stopper subunit and a second stopper subunit, wherein the first stopper subunit and the second stopper subunit prevent the at least two macrocylic components from unthreading from the threading component. In some embodiments, the threading component further comprises a first linking subunit and a second linking subunit, wherein the first linking subunit links a first end of the oligoviologen to the first stopper subunit and the second linking subunit links a second end of the oligoviologen to the second stopper subunit.

In some embodiments, the first linking subunit, the second linking subunit, or both the first linking subunit and the second linking subunit comprise an alkyl subunit. In particular embodiments, the first linking subunit, the second linking subunit, or both the first linking subunit and the second linking subunit comprise a C$_{3-9}$ alkyl subunit. In some embodiments, the first linking subunit, the second linking subunit, or both the first linking subunit and the second linking subunit comprise a polyethylene oxide subunit. In particular embodiments, the first linking subunit, the second linking subunit, or both the first linking subunit and the second linking subunit comprise a (O—CH$_2$—CH$_2$)$_{1-3}$ polyethylene oxide subunit.

In some embodiments, the first stopper subunit, the second stopper subunit, or both the first stopper subunit and the second stopper subunit comprise a triazole stopper subunit. In some embodiments, the first stopper, the second stopper, or both the first stopper and the second stopper comprise a triazole stopper moiety having a formula of R—C$_2$N$_3$—R', S', wherein R and R' are bulky moieties capable of preventing dethreading of the macrocyclic components. In particular embodiments, the first stopper subunit, the second stopper subunit, or both the first stopper subunit and the second stopper subunit comprise a (CH$_3$)$_3$C—CH$_2$—O—C(=O)—C$_2$N$_3$—C(=O)—O—CH$_2$—C(CH$_3$)$_3$ triazole stopper subunit.

In some embodiments, the rotaxane is complexed with an anion. In particular embodiments, the rotaxane is complexed with PF$_6^-$ or CF$_3$C(=O)O$^-$.

In some embodiments, the rotaxane is cationic. In some embodiments, the rotaxane is in a radical electronic state. In some embodiments, the rotaxane is in a radical cationic electronic state. In some embodiments, the rotaxane is capable of reversible oxidation and reduction.

In some embodiments, reducing the rotaxane contracts the nanoreactor and/or oxidizing the rotaxane extends the nanoactuator. In some embodiments, the nanoactuator is capable of reversible contraction and extension.

Another aspect of the invention is a method of actuating a nanoactuator, the method comprising oxidizing or reducing a nanoactuator as described above. In some embodiments, oxidizing the nanoactuator expands the nanoactuator. In some embodiments, reducing the nanoactuator contracts the nanoactuator.

Another aspect of the invention is a method of preparing a nanoactuator, the method comprising providing an oligoviologen and a CBPQT ring capable of forming an inclusion complex, wherein the oligoviologen is threaded through the CBPQT ring. The method may further comprise stoppering the oligoviologen. In some embodiments, the CBPQT is provided in excess of the oligoviologen. In some embodiments, the oligoviologen and the CBPQT is provided in the presence of Zn dust and/or MeCN. In some embodiments, the oligoviologen is stoppered by a Cu-free alkyne-azide cycloaddition.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 5A shows cyclic voltammograms of $4V^{8+}$ and an equimolar mixture of $4V^{8+}$ and $CBPQT^{4+}$. A glassy carbon working electrode, a platinum counter electrode, and a Ag/AgCl reference electrode were used in the characterization of 0.1 mM MeCN solutions of the oligoviologens at 298 K with 0.1 M $TBAPF_6$ serving as the electrolyte. A scan rate of 200 mV s$^{-1}$ was used in all analyses.

FIG. 5B shows cyclic voltammograms of $5V^{10+}$ and an equimolar mixture of $5V^{10+}$ and $CBPQT^{4+}$. A glassy carbon working electrode, a platinum counter electrode, and a Ag/AgCl reference electrode were used in the characterization of 0.1 mM MeCN solutions of the oligoviologens at 298 K with 0.1 M $TBAPF_6$ serving as the electrolyte. A scan rate of 200 mV s$^{-1}$ was used in all analyses.

FIG. 6A shows a simulated co-conformation of the oligopseudorotaxane $4V^{4(\cdot+)} \subset 2CBPQT^{2(\cdot+)}$ in different binding modes stabilized by radical-pairing interactions. The numbers (before the slash, in kcal mol$^{-1}$) show their relative energies, demonstrating that the co-conformation with the greatest number (after the slash) of $(BIPY^{\cdot+})_2$ pairs have the highest stability.

FIG. 6B shows a simulated co-conformation of the oligopseudorotaxane $4V^{4(\cdot+)} \subset 2CBPQT^{2(\cdot+)}$ in different binding modes stabilized by radical-pairing interactions. The numbers (before the slash, in kcal mol$^{-1}$) show their relative energies, demonstrating that the co-conformation with the greatest number (after the slash) of $(BIPY^{\cdot+})_2$ pairs have the highest stability.

FIG. 6C shows a simulated co-conformation of the oligopseudorotaxane $4V^{4(\cdot+)} \subset 2CBPQT^{2(\cdot+)}$ in different binding modes stabilized by radical-pairing interactions. The numbers (before the slash, in kcal mol$^{-1}$) show their relative energies, demonstrating that the co-conformation with the greatest number (after the slash) of $(BIPY^{\cdot+})_2$ pairs have the highest stability.

FIG. 6D shows a simulated co-conformation of the oligopseudorotaxane $4V^{4(\cdot+)} \subset 2CBPQT^{2(\cdot+)}$ in different binding modes stabilized by radical-pairing interactions. The numbers (before the slash, in kcal mol$^{-1}$) show their relative energies, demonstrating that the co-conformation with the greatest number (after the slash) of $(BIPY^{\cdot+})_2$ pairs have the highest stability.

FIG. 9A shows partial UV/Vis/NIR absorption spectra of MeCN solution of $4V^{4(\cdot+)}$ (c=10 μM) with 2 equiv, 10 equiv of $CBPQT^{2(\cdot+)}$ and oligorotaxane $3R|4BP^{8(\cdot+)}$.

FIG. 9B shows enlargement of the corresponding spectra in FIG. 9A from 800 to 1400 nm, indicating that mechanical bonds enhance molecular recognition.

FIG. 9C shows a partial UV/Vis/NIR absorption spectra of MeCN solution of $5V^{5(\cdot+)}$ (c=10 μM) with 2 equiv, 12 equiv of $CBPQT^{2(\cdot+)}$ and oligorotaxane $3R|5BP^{9(\cdot+)}$.

FIG. 9D shows enlargement of the corresponding spectra in FIG. 9C from 800 to 1400 nm, indicating that mechanical bonds enhance molecular recognition.

FIG. 10A shows a cyclic voltammogram of oligorotaxanes $3R|4BP^{16+}$. A glassy carbon working electrode, a platinum counter electrode, and a Ag/AgCl reference electrode were used in the characterization of 0.1 mM MeCN solutions of the oligoviologens at 298 K with 0.1 M TBAPF$_6$ serving as the electrolyte. A scan rate of 200 mV s$^{-1}$ was used in all the analyses.

FIG. 10B shows a cyclic voltammogram of oligorotaxanes 3R|5BP$^{18+}$. A glassy carbon working electrode, a platinum counter electrode, and a Ag/AgCl reference electrode were used in the characterization of 0.1 mM MeCN solutions of the oligoviologens at 298 K with 0.1 M TBAPF$_6$ serving as the electrolyte. A scan rate of 200 mV s$^{-1}$ was used in all the analyses.

FIG. 10C shows a cyclic voltammogram of 4V$^{8+}$ with 2 equiv of CBPQT$^{4+}$. A glassy carbon working electrode, a platinum counter electrode, and a Ag/AgCl reference electrode were used in the characterization of 0.1 mM MeCN solutions of the oligoviologens at 298 K with 0.1 M TBAPF$_6$ serving as the electrolyte. A scan rate of 200 mV s$^{-1}$ was used in all the analyses.

FIG. 10D shows a cyclic voltammogram of 5V$^{10+}$ with 2 equiv of CBPQT$^{4+}$. A glassy carbon working electrode, a platinum counter electrode, and a Ag/AgCl reference electrode were used in the characterization of 0.1 mM MeCN solutions of the oligoviologens at 298 K with 0.1 M TBAPF$_6$ serving as the electrolyte. A scan rate of 200 mV s$^{-1}$ was used in all the analyses.

FIG. 10E shows a cyclic voltammogram of 4V$^{8+}$ with 7 equiv of CBPQT$^{4+}$. A glassy carbon working electrode, a platinum counter electrode, and a Ag/AgCl reference electrode were used in the characterization of 0.1 mM MeCN solutions of the oligoviologens at 298 K with 0.1 M TBAPF$_6$ serving as the electrolyte. A scan rate of 200 mV s$^{-1}$ was used in all the analyses.

FIG. 10F shows a cyclic voltammogram of 5V$^{10+}$ with 7 equiv of CBPQT$^{4+}$. A glassy carbon working electrode, a platinum counter electrode, and a Ag/AgCl reference electrode were used in the characterization of 0.1 mM MeCN solutions of the oligoviologens at 298 K with 0.1 M TBAPF$_6$ serving as the electrolyte. A scan rate of 200 mV s$^{-1}$ was used in all the analyses.

FIG. 17A shows a $^1$H-$^1$H gCOSY spectrum (500 MHz, CD$_3$COCD$_3$, 298K) of oligorotaxane 3R|4BP•16PF$_6$.

FIG. 17B shows a $^1$H-$^1$H gCOSY spectrum (500 MHz, CD$_3$COCD$_3$, 298K) of oligorotaxane 3R|4BP•16PF$_6$.

FIG. 19A shows a $^1$H-$^1$H gCOSY spectrum (500 MHz, CD$_3$COCD$_3$, 298K) of oligorotaxane 3R|5BP•18PF$_6$.

FIG. 19B shows a $^1$H-$^1$H gCOSY spectrum (500 MHz, CD$_3$COCD$_3$, 298K) of oligorotaxane 3R|5BP•18PF$_6$.

FIG. 20 shows a partial $^1$H NMR spectrum (400 MHz, CD$_3$COCD$_3$, 233K) of oligorotaxane 3R|5BP•18PF$_6$.

FIG. 21A shows a analytical RP-HPLC chromatograms (H$_2$O-MeCN, 0.1% TFA, 0-100% MeCN in 60 min, λ=254 nm) of 3R|4BP•16PF$_6$.

FIG. 21B shows a analytical RP-HPLC chromatograms (H$_2$O-MeCN, 0.1% TFA, 0-100% MeCN in 60 min, λ=254 nm) of 3R|5BP•18PF$_6$. The higher charged oligorotaxane 3R|5BP•18PF$_6$ has a shorter retention time on the column.

FIG. 22A shows an experimental HRMS (ESI) spectra of 3R|4BP•16PF$_6$. Calculated for $C_{176}H_{188}F_{78}N_{22}O_8P_{13}$: 1540.6775 [M-3PF$_6$]$^{3+}$.

FIG. 22B shows a simulated HRMS (ESI) spectra of 3R|4BP•16PF$_6$. Calculated for $C_{176}H_{188}F_{78}N_{22}O_8P_{13}$: 1540.6775 [M-3PF$_6$]$^{3+}$.

FIG. 22C shows an experimental and simulated HRMS (ESI) spectra of 3R|5BP•18PF$_6$. Calculated for $C_{194}H_{204}F_{90}N_{24}O_8P_{15}$: 1724.7741 [M-3PF$_6$]$^{3+}$.

FIG. 22D shows a simulated HRMS (ESI) spectra of 3R|5BP•18PF$_6$. Calculated for $C_{194}H_{204}F_{90}N_{24}O_8P_{15}$: 1724.7741 [M-3PF$_6$]$^{3+}$.

FIG. 23A shows determination of binding stoichiometry of CBPQT$^{2(•+)}$ with respect to 4V$^{4(•+)}$ in MeCN using the method of continuous variation with a Job plot showing the intensity of the trisradical absorption band attributable to 4V$^{4(•+)}$⊂2CBPQT$^{2(•+)}$ host-guest complex against χ, which represents the CBPQT$^{2(•+)}$:4V$^{4(•+)}$ molar ratio.

FIG. 23B shows determination of binding stoichiometry of CBPQT$^{2(•+)}$ with respect to 4V$^{4(•+)}$ in MeCN using the method of continuous variation with absorption spectroscopy data used in the Job plot. The spectra were recorded at 298 K with [CBPQT$^{2(•+)}$]+[4V$^{4(•+)}$]=50 μM.

FIG. 24A shows determination of binding stoichiometry of CBPQT$^{2(•+)}$ with respect to 5V$^{5(•+)}$ in MeCN using the method of continuous variation with a Job plot showing the intensity of the trisradical absorption band attributable to 5V$^{5(•+)}$⊂2CBPQT$^{2(•+)}$ host-guest complex against χ, which represents the CBPQT$^{2(•+)}$:5V$^{5(•+)}$ molar ratio. (b) Absorption spectroscopy data used in the Job plot. The spectra were recorded at 298 K with [CBPQT$^{2(•+)}$]+[5V$^{5(•+)}$]=50 μM.

FIG. 24B shows determination of binding stoichiometry of CBPQT$^{2(•+)}$ with respect to 5V$^{5(•+)}$ in MeCN using the method of continuous variation with absorption spectroscopy data used in the Job plot. The spectra were recorded at 298 K with [CBPQT$^{2(•+)}$]+[5V$^{5(•+)}$]=50 μM.

DEFINITIONS

Figure 1:
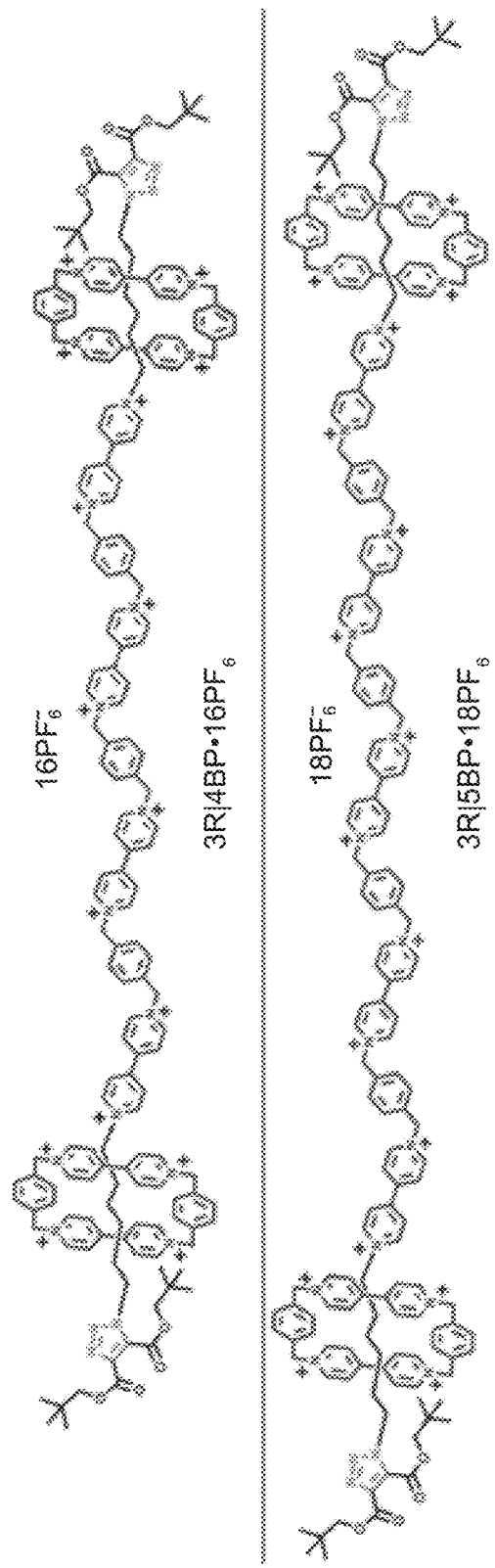
FIG. 1 shows structural formulae of the oligorotaxanes 3R|4BP•16PF6 and 3R|5BP•18PF6 composed of only positively charged components.

"Bridging subunit" (B) means a subunit that links viologen subunits to form an oligoviologen. Bridging subunit include p-xylene briding subunits.

"Linking subunit" (L) means a subunit capable of linking an oligioviologen with a stopper subunit. An oligoviologen and one or more linking subunits may together form the threading component of a rotaxane or pseudorotaxe.

"Macrocyclic component" (MC) means a molecule that has at least one ring (cycle) large enough to allow it to be threaded onto a linear subchain of another molecule. Macrocylic components include cyclobis(paraquat-p-phenylene) (CBPQT).

"Nanoacuator" means a molecular component responsible for moving or controlling a mechanism or system. When a control signal is received, the nanoactuator responds with mechanical motion. For example, when an electrochemical signal is received by a nanoactuator, the nanoactuator may respond by extending or contracting.

"Oligoviologen" (OV) means a component having different numbers of viologen subunits (V) linked with a bridging subunit. Oligoviologens may include 4,4'-bipyridinium (BIPY) subunits are linked by p-xylene bridging subunits. Oligoviologens may be described by the number of viologen subunits. For example, 4V may describe an oligoviologen having four BIPY subunits linked with three p-xylene bridging subunits or 5V may describe an oligoviologen having five BIPY subunits linked with four p-xylene bridging subunits. Oligoviologens may be threading components for a rotaxane or a pseudorotaxe.

"Pseudorotaxane" means a rotaxane-like molecular assembly in which the threading component(s) has(have) ends small enough to permit threading or dethreading of the macrocyclic component(s). A pseudorotaxane may be an "oligopseudorotaxane" when it comprises an oligomeric threading component. Pseudorotaxes may include unstoppered oligoviolgen threading components threaded through one or more macrocyclic components. Particular psuedorotaxens include $4V \subset 2CBPQT$ and $5V \subset 2CBPQT$.

"Rotaxane" means a complex molecular assembly comprising at least one molecule with a linear section threaded through at least one macrocyclic part of another or the same molecule, and having end-groups large enough to prevent dethreading of the macrocyclic component. A rotaxane may be an "oligorotaxane" when it comprises an oligomeric threading component. Rotaxes may include stoppered oligoviolgen threading components threaded through one or more macrocyclic components. Particular rotaxanes include 3R|4BP and 3R|5BP.

"Stopper subunit" (S) means a group bulky enough to prevent dethreading of a given macrocyclic component from a threading component or its translocation to another linear section of the threading component.

"Threading component" (TC) means a molecule with at least one linear section onto which at least one macrocyclic component is threaded. A threading component may be an "oligomeric threading component" when it comprises repeating subunits.

"Viologen subunit" (V) means a subunit that is derivative of 4,4'-bipyridine ($C_{10}H_8N_2$). Viologens include 4,4'-bipyridinium (BIPY) subunits.

DETAILED DESCRIPTION

Provided herein are nanoactuators capable of receiving a control signal and responding with mechanical motion. The nanoactuators disclosed herein comprise foldameric rotaxanes based on a strategy for creating foldameric oligorotaxanes composed of only positively charged components. The rotaxanes comprise threading components comprised of oligoviologens in which different numbers of 4,4'-bipyridinium ($BIPY^{2+}$) subunits are linked by p-xylene bridges, and the treading components are shown to be capable of being threaded by cyclobis(paraquat-p-phenylene) ($CBPQT^{4+}$) rings following the introduction of radical-pairing interactions under reducing conditions. UV/Vis/NIR Spectroscopic and electrochemical investigations suggest that the reduced oligopseudorotaxanes fold into highly ordered secondary structures as a result of the formation of $BIPY^{\cdot+}$ radical cation pairs. Furthermore, by installing bulky stoppers at each end of the oligopseudorotaxanes by means of Cu-free alkyne-azide cycloadditions, their analogous oligorotaxanes, which retain the same stoichiometries as their progenitors, can be prepared. Solution-state studies of the oligorotaxanes indicate that their mechanically interlocked structures lead to the enforced interactions between the dumbbell and ring components, allowing them to fold (contract) in their reduced states and unfold (expand) in their fully oxidized states as a result of Coulombic repulsions. This electrochemically controlled reversible folding and unfolding process, during which the oligorotaxanes experience length contractions and expansions, is reminiscent of the mechanisms of actuation associated with muscle fibers.

There are a number of potential application for these rotaxanes. Examples of application include, but are not limited to, electrochemically responsive artificial molecular muscles, electronic information storage devices, functional molecular actuators, organic molecular switches, semiconducting organic radical materials, shape memory materials.

A number of advantages can be realized from these rotaxanes. The actuations of the oligorotaxanes can be achieved by both chemical and electrochemical stimuli. The actuation of the oligorotaxanes are less influenced by changes in concentrations in solution. Introduction of the mechanical bond further regulates the co-conformations of the oligorotaxanes. Radical-pairing interactions provide stronger conformational control than analogous donor-acceptor based systems. Moreover, coulombic repulsions force the secondary structures of the oligorotaxanes to extend, improving the working efficiency.

Herein we describe a new class of functional foldameric oligorotaxanes composed of only positively charged components whose construction rely on the interactions between the oligoviologens threads and the $CBPQT^{4+}$ ring under reducing conditions. Structural formulae of exemplary rotaxes are provided in FIG. 1. This design is based on the consideration that, unlike the donor-acceptor-based examples wherein the folded secondary structures are "permanent" aside from the influence of solvent and temperature, the radical-pairing interactions enable the co-conformations of the resulting oligorotaxanes to be switched reversibly between folded and unfolded states by altering the external potential. Specifically, in their oxidized states, the positively charged dumbbells apparently become extended and the $CBPQT^{4+}$ rings are repelled from each other and also from the dumbbells as a result of Coulombic repulsion. Upon reduction back to their radical states, however, solution studies indicate the formation of folded structures driven by radical-pairing interactions. This reversible process, which switches the interactions of bipyridinium units between being repulsive and attractive and giving rise to the extension and contraction of the oligorotaxane chains, can lead to drastic changes in their lengths. This property makes it possible for us to control the operation of artificial molecular motors. The relative movements of the components in these oligorotaxanes, at the behest of external stimuli, are reminiscent of the actions of macroscopic springs.[34] In addition, these molecular-level movements, resembling those of the workings of muscle tissue, can potentially be developed further in the context of artificial molecular muscles that respond to electrochemical stimuli. [35-39]

Figure 2:
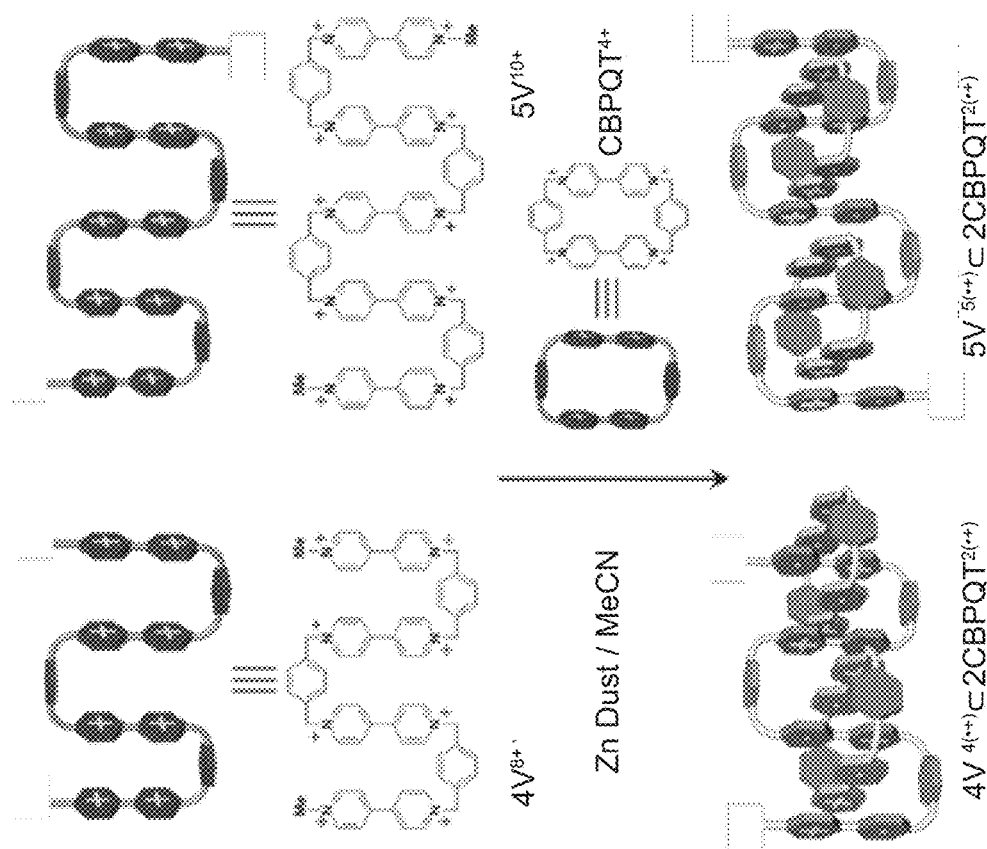
FIG. 2 shows structural formulas and graphical representations of the oligopseudorotaxanes $4V^{4(\cdot+)} \subset 2CBPQT^{2(\cdot+)}$ and $5V^{5(\cdot+)} \subset 2CBPQT^{2(\cdot+)}$ formed as a result of radical-pairing interactions.

Precise designs of molecular components are necessary in order to optimize noncovalent bonding interactions required for the efficient production of MIMs employing template-directed strategies. We have demonstrated that strong intra- and intermolecular radical-pairing interactions come into play upon reduction of linear oligoviologen chains in which the dicationic $BIPY^{2+}$ units are separated periodically by xylene linkers, rendering them to fold both in solution and in the solid-state. [40] It should be emphasized, however, that the nature of the folded (super)structures of these oligoviologens are either susceptible to changes in concentration or (ii) lack imposed linear geometries, i.e., they can form loops, which limits their potential applications at least as far as serving as a prototype for artificial molecular muscles is concerned. As a consequence, it is of paramount importance to introduce ring components on to the oligoviologens in order to arrest the chains self-entangling and further regulate the folded secondary superstructures so that they are (i) less influenced by changes in concentration since they are MIMs, and obliged to adopt linear geometries. On the basis of these considerations, we have chosen oligoviologens with four and five $BIPY^{2+}$ units—namely $4V^{8+}$ and $5V^{10+}$—to serve as the linear components of the oligorotaxanes (FIG. 2), since (iii) their self-folding tendencies[40] under reducing conditions are less pronounced, when compared with their longer analogues, making it possible for them to interact with the rings to form the desired oligorotaxanes, while (iv) compared with their shorter analogues, they can potentially bind more $CBPQT^{2(\cdot+)}$ rings under reducing conditions, a situation which is expected to provide additional (co)-conformational control during the folding and unfolding processes by (v) generating more $BIPY^{\cdot+}$ recognition sites to stabilize their radical-state superstructures, and (vi) providing stronger Coulombic repulsion so as to force the secondary structures to become extended upon oxidation.

Figure 3A:
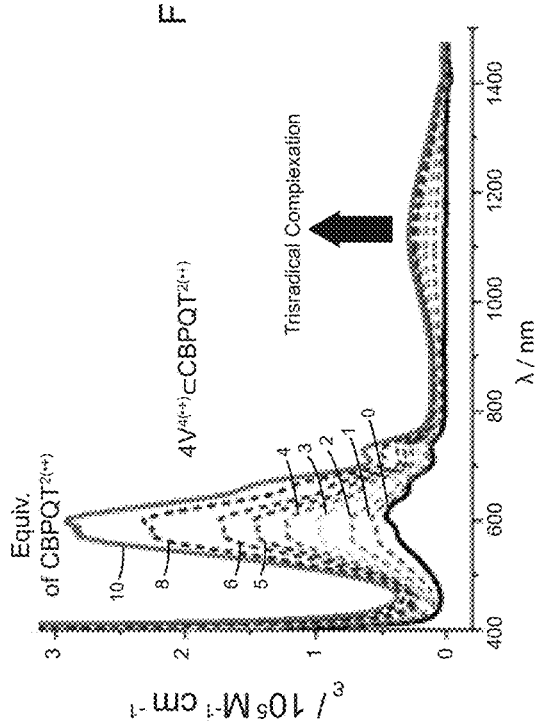
FIG. 3A shows UV/Vis/NIR Absorption spectrophotometric titration of $4V^{4(\cdot+)}$ by $CBPQT^{2(\cdot+)}$. Solvent: MeCN; black: $[4V^{4(\cdot+)}]=10\ \mu M$; purple: $(CBPQT^{2(\cdot+)})/(4V^{4(\cdot+)})=10$.
Figure 3B:
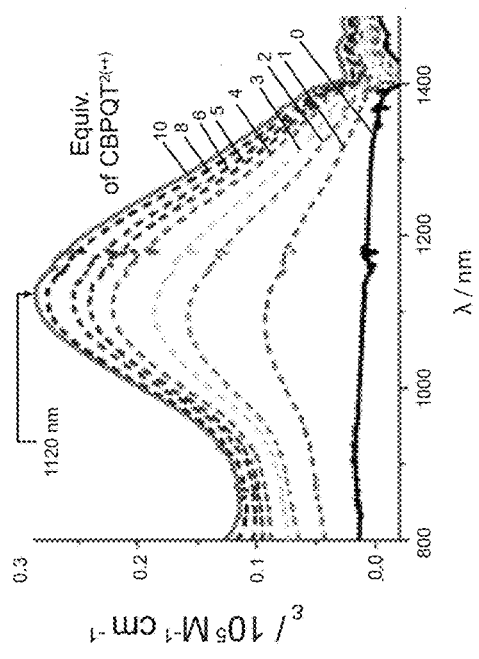
FIG. 3B shows an enlargement of the spectra shown in FIG. 3A from 800 to 1500 nm. The rising peak intensity observed at 1120 nm upon titration indicates the formation of the trisradical inclusion complexes.

As the key intermediates in the construction of these oligorotaxanes, the formation (FIG. 2) of the oligopseudorotaxanes between the reduced oligoviologens—namely $4V^{4(\cdot+)}$ and $5V^{5(\cdot+)}$—and the $CBPQT^{2(\cdot+)}$ ring, was first of all investigated (FIGS. 3A and 3B) by performing UV/Vis/NIR titrations. Following the reduction of the oligoviologen $4V^{8+}$ to its radical cationic state by Zn dust, the absorption spectrum of a MeCN solution of $4V^{4(\cdot+)}$ (10 μM) was recorded at room temperature. Next, an increasing amount of $CBPQT^{2(\cdot+)}$ from 1 to 10 equiv was titrated into this MeCN solution and the UV/Vis/NIR spectra were recorded. The results reveal (FIGS. 3A and 3B) that, when only $4V^{4(\cdot+)}$ is present in the solution, an absorption band around 900 nm is observed, indicating the formation of $BIPY^{\cdot+}$ dimers induced by intramolecular radical-pairing interactions.[40] Upon the addition of $CBPQT^{2(\cdot+)}$, however, a new absorption band emerges (FIGS. 3A and 3B) centered on 1110 nm, which clearly indicates the formation of trisradical complexes. [41] As the concentration of $CBPQT^{2(\cdot+)}$ in the solution increases, the intensity of the trisradical band grows with a gradual decrease in its intensity increment until finally a saturation point is reached, a situation which suggests the maximum number of $BIPY^{\cdot+}$ units on the $4V^{4(\cdot+)}$ have been encircled by the $CBPQT^{2(\cdot+)}$ rings. It is also noteworthy that this absorption band is significantly red-shifted, compared (1066 nm) with the example of the inclusion complex $MV^{\cdot+} \subset CBPQT^{2(\cdot+)}$ between reduced methyl viologen ($MV^{\cdot+}$) and [32] This observation possibly comes about because of the fact that $4V^{4(\cdot+)}$ binds multiple $CBPQT^{2(\cdot+)}$ rings in solution, such that the resulting radical pairs interact with each other intermolecularly through space to form (FIG. 2) a continuous π-stack, giving rise to a narrower electron-migrating energy gap—in other words, a red-shifted absorption.

Figure 4A:
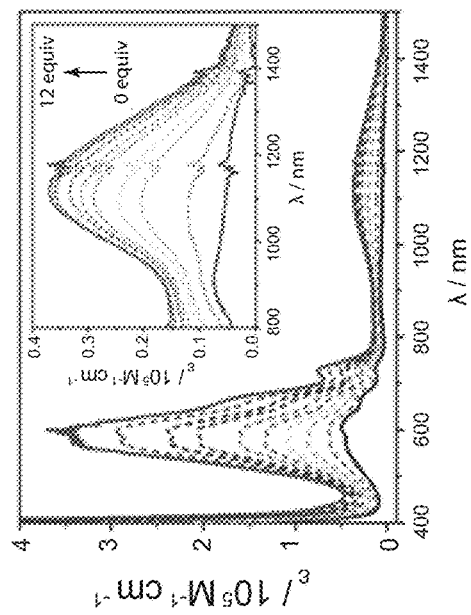
FIG. 4A shows UV/Vis/NIR Absorption spectrophotometric titration experiment of $5V^{5(\cdot+)}$ by $CBPQT^{2(\cdot+)}$ 298 K. Solvent: MeCN; black: $[5V^{5(\cdot+)}]=10\ \mu M$; purple: c ($CBPQT^{2(\cdot+)}$)/c ($5V^{5(\cdot+)}$)=12.
Figure 4B:
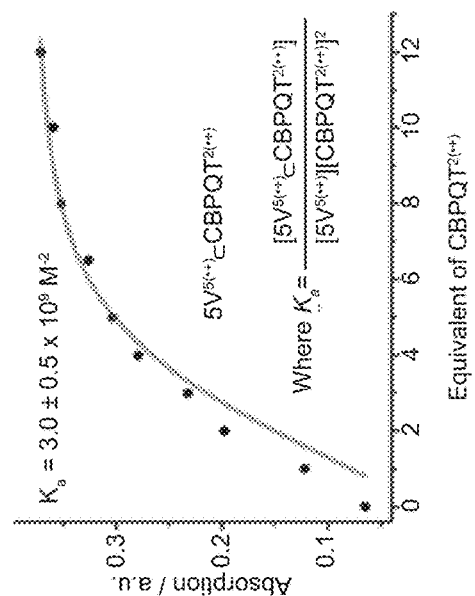
FIG. 4B shows the simulated curve for the determination of the binding constant between $5V^{5(\cdot+)}$ and $CBPQT^{2(\cdot+)}$.

A similar phenomenon was observed in the case of $5V^{5(\cdot+)}$, where an absorption band, centered on 1140 nm, emerges (FIG. 4A) immediately after the addition of $CBPQT^{2(\cdot+)}$, indicating rapid formation of trisradical inclusion complexes. It is worth noting that the absorption band in the case of $5V^{5(\cdot+)}$ is further red-shifted with respect to that observed in the case of $4V^{4(\cdot+)}$, presumably because of the participation of an additional $BIPY^{\cdot+}$ subunit in the π-stack results (FIG. 2) in a stacked superstructure of even greater length. All these observations suggest that the $CBPQT^{2(\cdot+)}$ rings interact strongly with both $4V^{4(\cdot+)}$ and $5V^{5(\cdot+)}$, in spite of the existence of competitive intramolecular radical-pairing interactions within $4V^{4(\cdot+)}$ and $5V^{5(\cdot+)}$ themselves. This situation possibly pertains because $BIPY^{\cdot+}$ units prefer to stack in a face-to-face manner in solution, and the $CBPQT^{2(\cdot+)}$ rings, whose rigid geometry already dictates that two $BIPY^{\cdot+}$ units be parallel, facilitates this type of stacking fashion.

In order to determine the binding stoichiometry between both the reduced oligoviologens $4V^{4(\cdot+)}$ and $5V^{5(\cdot+)}$, and $CBPQT^{2(\cdot+)}$, Job plots were performed. The titrations reveal that $CBPQT^{2(\cdot+)}$ forms 2:1 complexes with both $4V^{4(\cdot+)}$ and $5V^{5(\cdot+)}$ in MeCN solutions, confirming the formation of the oligopseudorotaxanes. According to this binding stoichiometry, we found that the stronger interactions between $CBPQT^{2(\cdot+)}$ and $4V^{4(\cdot+)}$, as well as between $CBPQT^{2(\cdot+)}$ and $5V^{5(\cdot+)}$, compared to the self-dimerization of $4V^{4(\cdot+)}$ and $5V^{5(\cdot+)}$, are also supported by the results of DFT calculations. The formation enthalpies ($\Delta H$) of the inclusion complex $4V^{4(\cdot+)} \subset 2CBPQT^{2(\cdot+)}$ and $5V^{5(\cdot+)} \subset 2CBPQT^{2(\cdot+)}$ are 66.1 and 73.6 kcal mol-1, whereas the $\Delta H$ values for the $4V^{4(\cdot+)}$ and $5V^{5(\cdot+)}$ dimers are only 42.7 and 48.4 kcal mol-1, respectively, indicating that the organized geometry provided by the $CBPQT^{2(\cdot+)}$ rings amount to approximately 24 kcal mol-1 stabilizing energy. More importantly, these 2:1 binding stoichiometries support the formation of favorable radical-pairing interactions between all of the BIPY·+ units in both the oligoviologens and the $CBPQT^{2(\cdot+)}$ rings—a co-conformation which is in a good agreement with the red-shifted band observed in the UV/Vis/NIR spectra—as a consequence of the assembly (FIG. 2) of well-defined secondary structures. Furthermore, the binding constants between reduced oligoviologens and $CBPQT^{2(\cdot+)}$ were calculated, demonstrating both $4V^{4(\cdot+)}$ and $5V^{5(\cdot+)}$ bind strongly ($K_a \sim 10^9 M^{-2}$) with two $CBPQT^{2(\cdot+)}$ rings in solution.

In order to elucidate the binding mechanism between the reduced oligoviologens and $CBPQT^{2(\cdot+)}$, cyclic voltammetry (CV) was also performed. The CV (FIG. 5A) of an equimolar mixture of $4V^{8+}$ and $CBPQT^{4+}$ reveals the presence of a single reduction peak (−300 mV, peak potential) leading to the radical species. Indeed, six electrons are involved in this reduction process: two electrons go into the $CBPQT^{4+}$ ring, forming the diradical dication $CBPQT^{2(\cdot+)}$, and four electrons go to $4V^{8+}$, forming the tetraradical tetracation $4V^{4(\cdot+)}$. As a consequence of this simultaneous six-electron process, formation of the $4V^{4(\cdot+)} \subset CBPQT^{2(\cdot+)}$ inclusion complex occurs spontaneously. It is noteworthy that the reduction potential at −300 mV is cathodically shifted significantly, compared with those for the individual $4V^{8+}$ oligomer (at −330 mV) and the $CBPQT^{4+}$ rings (at −360 mV)[29], i.e., the mixture is easier to reduce, indicating that the formation of the inclusion complex stabilizes the radical species. On re-oxidation, the result is that one of the BIPY·+ radical cations of the complexed $CBPQT^{2(\cdot+)}$ associates more weakly with the $4V^{4(\cdot+)}$ than the other BIPY·+, leading to the conclusion that the oxidation of this inclusion complex occurs in a stepwise manner, with the weaker interacting BIPY·+ in the $CBPQT^{2(\cdot+)}$ ring and the unpaired BIPY·+ in $4V^{4(\cdot+)}$ being oxidized first of all at a potential at −209 mV, leaving the strongly interacting BIPY·+ subunits to become oxidized at more positive potentials, i.e., +32 mV.

In the case of $5V^{10+}$ and $CBPQT^{4+}$, an equimolar mixture also gives (FIG. 5B) a more positive reduction potential at −264 mV, compared with those of their individual components, indicating the formation of the inclusion complex. More significantly, when the inclusion complex is undergoing oxidation, it registers the first potential at −205 mV, a value which is close to that of the inclusion complex between $4V^{8+}$ and $CBPQT^{4+}$, indicating that the unpaired BIPY·+ radical cations have a similar tendency to become oxidized. By contrast, the second potential is shifted slightly to +45 mV, presumably because the presence of an additional BIPY·+ radical cation makes the dissociation between $5V^{5(\cdot+)}$ and $CBPQT^{2(\cdot+)}$ even more difficult.

Computational studies were carried out in order to demonstrate how the superstructures of the oligopseudorotaxanes are regulated by radical-pairing interactions. In the case of $4V^{4(\cdot+)} \subset 2CBPQT^{2(\cdot+)}$, we examined four possible co-conformations, and discovered that the one (FIG. 6A) incorporating two $CBPQT^{2(\cdot+)}$ rings which are centered on the first and the third BIPY·+ subunits, that allows all the BIPY·+ radical cations, in both $4V^{4(\cdot+)}$ and in the $CBPQT^{2(\cdot+)}$ rings to stack employing a total of seven (BIPY·+)$_2$ radical pairs, has the highest stability. The open superstructures with the middle BIPY·+ subunit in $4V^{4(\cdot+)}$ twisted away (FIGS. 6B-C), which releases some strain at the angle of BIPY·+-paraxylene-BIPY·+ in $4V^{4(\cdot+)}$, is not sufficient to compensate for the loss of one radical pair—leaving six (BIPY·+)$_2$ radical pairs in total—between the BIPY·+ radical cations, rendering them much higher energy (2~7 kcal mol$^{-1}$) co-conformations.

Figure 7A:
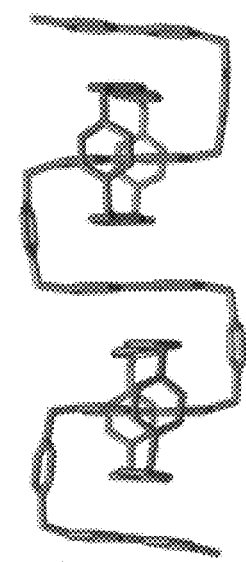
FIG. 7A shows a simulated co-conformation of the oligopseudorotaxane $5V^{5(\cdot+)} \subset 2CBPQT^{2(\cdot+)}$ in different binding modes stabilized by radical-pairing interactions. The numbers (black, in kcal mol$^{-1}$) show their relative energies, demonstrating that the co-conformation with the greatest number (red) of $(BIPY^{\cdot+})_2$ pairs have the highest stability.
Figure 7B:
FIG. 7B shows a simulated co-conformation of the oligopseudorotaxane $5V^{5(\cdot+)} \subset 2CBPQT^{2(\cdot+)}$ in different binding modes stabilized by radical-pairing interactions. The numbers (black, in kcal mol$^{-1}$) show their relative energies, demonstrating that the co-conformation with the greatest number (red) of $(BIPY^{\cdot+})_2$ pairs have the highest stability.
Figure 7C:
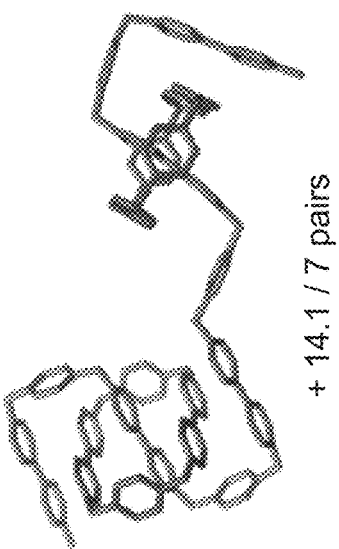
FIG. 7C shows a simulated co-conformation of the oligopseudorotaxane $5V^{5(\cdot+)} \subset 2CBPQT^{2(\cdot+)}$ in different binding modes stabilized by radical-pairing interactions. The numbers (black, in kcal mol$^{-1}$) show their relative energies, demonstrating that the co-conformation with the greatest number (red) of $(BIPY^{\cdot+})_2$ pairs have the highest stability.
Figure 7D:
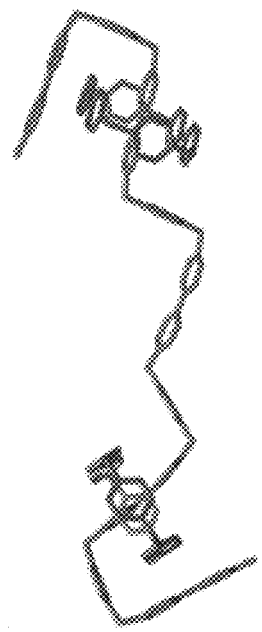
FIG. 7D shows a simulated co-conformation of the oligopseudorotaxane $5V^{5(\cdot+)} \subset 2CBPQT^{2(\cdot+)}$ in different binding modes stabilized by radical-pairing interactions. The numbers (black, in kcal mol$^{-1}$) show their relative energies, demonstrating that the co-conformation with the greatest number (red) of $(BIPY^{\cdot+})_2$ pairs have the highest stability.

Four co-conformations of $5V^{5(\cdot+)} \subset 2CBPQT^{2(\cdot+)}$, where the one with the largest number of (BIPY·+)$_2$ pairs is (FIG. 7A) the most stable co-conformation, constitutes a result which is in a good agreement with $4V^{4(\cdot+)} \subset 2CBPQT^{2(\cdot+)}$. It is also noteworthy that, compared with the $4V^{4(\cdot+)} \subset 2CBPQT^{2(\cdot+)}$ superstructure, once the continuous BIPY·+ stacking is interrupted in the case of $5V^{5(\cdot+)} \subset 2CBPQT^{2(\cdot+)}$, the resulting co-conformations (FIGS. 7B-C) are significantly more destabilized (10.0, 14.1 and 20.2 kcal mol$^{-1}$), indicating that the π-π stacking contributes to the stabilization energy. These observations can be rationalized by the presence of a continuous π-π stack, in which all the orbitals can interact with each other, leading to a lower orbital binding energy. In the case of the longer π-π stack, $5V^{5(\cdot+)} \subset 2CBPQT^{2(\cdot+)}$, this effect is even more pronounced. The computational investigations also reveal how the number of BIPY·+ subunits affects the secondary structures of the possible co-conformations, providing a unique example where longer oligoviologens have a higher tendency of folding.

Figure 8:
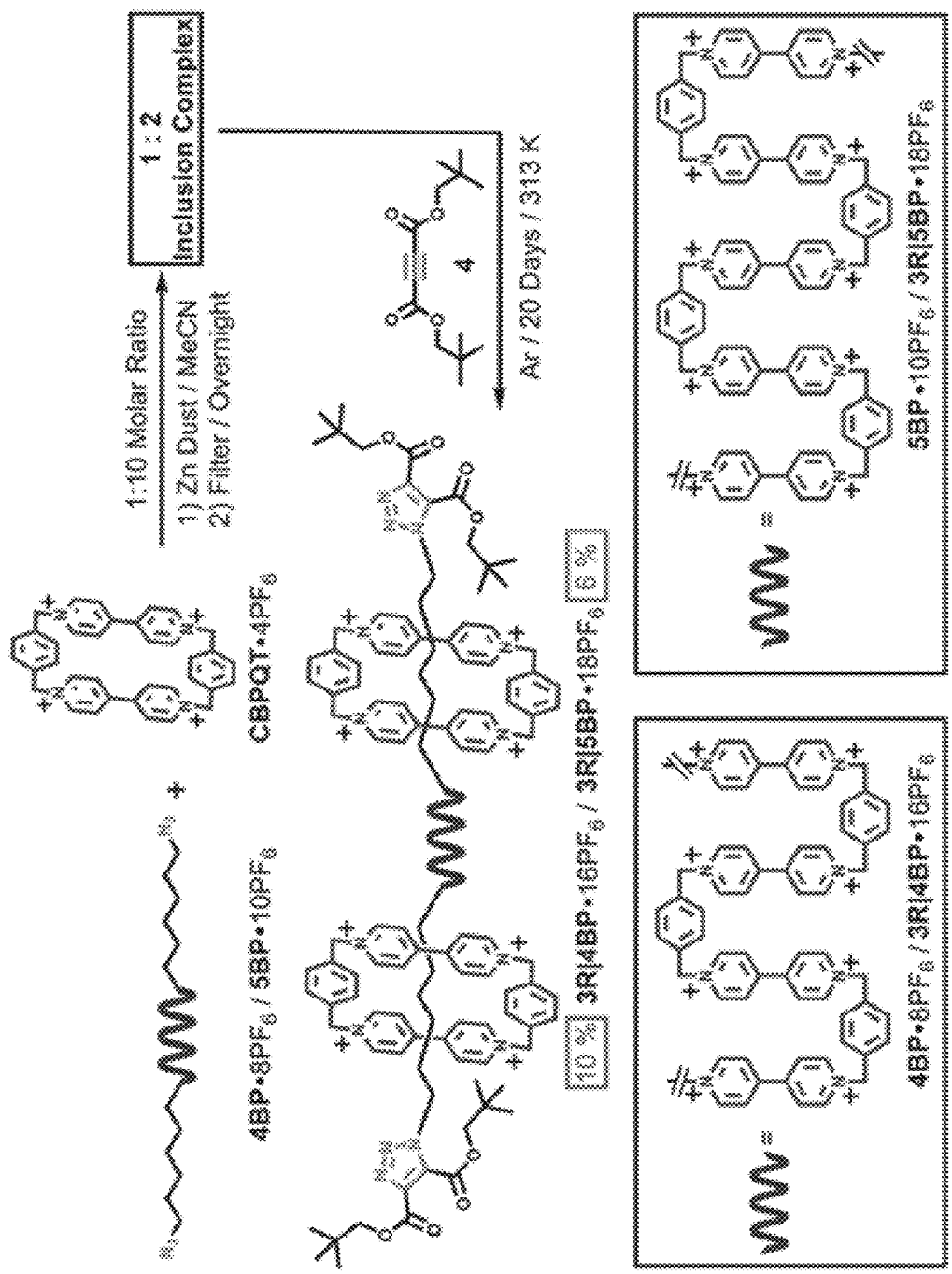
FIG. 8 shows syntheses of oligorotaxanes $3R|4BP^{16+}$ and $3R|5BP^{18+}$ by radical templation using Cu-free alkyne-azide cycloadditions.

Having shown that both of oligopseudorotaxanes prefer a highly ordered secondary structures in solution, we decided to investigate whether this behavior can be promoted in the case of the oligorotaxanes and so facilitate potential applications. Therefore, we carried out the syntheses of the oligorotaxanes, which rely on the templation present in their oligopseudorotaxane progenitors. In the beginning, an azide group is attached, by means of hexamethylene chain linkers to each end of the oligoviologens. These linkers are expected to be long enough to act as collecting zones for the $CBPQT^{4+}$ rings in their fully oxidized states. The azide-functionalized oligoviologens are then mixed with a gross excess (10 equiv) of $CBPQT^{4+}$ in MeCN under an Ar atmosphere. Upon reduction to their radical cationic states, the solutions turn, first of all, to dark blue and then, after a few minutes, to an intense purple color, indicating the formation of the inclusion complexes. After stirring the solutions overnight to allow the formation of the inclusion complexes to reach thermodynamic equilibrium, a bulky alkyne 4, which acts as the stopper precursor, is added and the solutions are stirred for a further 20 days. The highly charged oligorotaxanes, 3R|4BP•16PF$_6$ and 3R|5BP•18PF$_6$, were isolated (FIG. 8) from the corresponding reaction mixtures by preparative-HPLC in yields[43] of 10 and 6%, respectively. $^1$H NMR and $^1$H-$^1$H COSY spectra show (See SI, Section 3) that the $CBPQT^{4+}$ rings become located, after oxidation, on the hexamethylene chains as a result of Coulombic repulsions, as evidenced by the significantly lower resonating frequencies (<0 ppm) of protons on the hexamethylene chains. Therefore, it is apparent that 3R|4BP$^{16+}$ and 3R|5BP$^{18+}$ are fully stretched in their oxidized states. It is also noteworthy that both the oligorotaxanes 3R|4BP$^{16+}$ and 3R|5BP$^{18+}$ are composed of one oligoviologen dumbbell and two $CBPQT^{4+}$ rings, as confirmed by the $^1$H NMR integration and high resolution mass spectrometry (HR-MS). The outcome is also consistent with the solution-state experiments performed on the oligopseudorotaxanes, demonstrating that the binding stoichiometries are retained during the production of the oligorotaxanes, in spite of the fact that the constitutions of oligoviologens are slightly different.

With the two oligorotaxanes 3R|4BP$^{16+}$ and 3R|5BP$^{18+}$ in hand, we then set out to investigate the behavior of their radical cationic states—namely 3R|4BP$^{8(\bullet+)}$ and 3R|5 BP$^{9(\bullet+)}$—in MeCN solutions. The comparison of their UV/Vis/NIR spectra (FIGS. 9A-9D) with those of the oligopseudorotaxanes shows that, while the peaks around 600 nm still remain (FIGS. 9A and 9C) a feature characteristic of the free CBPQT$^{2(\bullet+)}$ rings in the case of oligopseudorotaxane, they are replaced by blue-shifted absorption bands centered on 550 nm, in the case of 3R|4BP$^{8(\bullet+)}$ and 3R|5 BP$^{9(\bullet+)}$, an observation which is typical of strong BIPY$^{\bullet+}$ radical pimerization.[44] This absorption peak assignment is further confirmed by a variable-temperature UV/Vis/NIR experiment. Moreover, the absorption intensities of the trisradical bands of 3R|4BP$^{8(\bullet+)}$ and 3R|5BP$^{9(\bullet+)}$ are significantly higher (FIGS. 9B and 9D) than those of the 1:2 molar mixtures of (i) 4V$^{4(\bullet+)}$ and (ii) 5V$^{5(\bullet+)}$ with CBPQT$^{2(\bullet+)}$, despite their almost identical chemical compositions. Indeed, we found that the absorption intensities are close to those of the saturated situations in the cases of oligopseudorotaxanes. These observations suggest that the molecular recognition between 4V$^{4(\bullet+)}$, 5V$^{5(\bullet+)}$ and CBPQT$^{2(\bullet+)}$, along with the strengths of the radical-pairing interactions are enhanced on account of the interlaced superstructures, which restrict the motions of the CBPQT$^{2(\bullet+)}$ rings so that they rest exclusively along the oligoviologen chains, facilitating the folding process.

In order to gain a deeper insight into the mechanically interlocked structures and understand the properties of the radical-radical pairing recognition between the interlocked dumbbells and ring components, we performed (FIGS. 10A-10B) CV experiments on the oligorotaxanes 3R|4BP$^{16+}$ and 3R|5BP$^{18+}$ and compared the results with those obtained (FIGS. 10C-10F) using the oligopseudorotaxanes. It turns out (FIGS. 10A-10B) that the CV profiles of the oligorotaxanes display three reduction peaks with potentials at −60, −190 and −271 mV for 3R|4BP$^{16+}$ and at 0, −174 and −273 mV for 3R|5BP$^{18+}$. The two additional reduction peaks in both cases, whose potentials are shifted toward positive values compared with those of their oligopseudorotaxane progenitors, can be interpreted in terms of a stepwise formation of the (BIPY$^{\bullet+}$)$_n$ pairs in 3R|4BP$^{16+}$ and 3R|5BP$^{18+}$ upon reduction. In the case of 3R|4BP$^{16+}$, all the BIPY$^{2+}$ units experience repulsion in its fully oxidized state. Upon reduction, a two-electron process is observed at a potential of 60 mV. Considering that the 4V$^{8+}$ dumbbell has a higher reduction potential than the CBPQT$^{4+}$ rings, we believe that both these electrons go preferentially into the dumbbell components in order to relief the repulsion between the BIPY$^{2+}$ units. Subsequently the oligorotaxane accepts another two electrons at a potential of 190 mV, whereupon both rings become reduced to CBPQT$^{2+(\bullet+)}$, leading to the translation from the hexamethylene chains to the BIPY$^{\bullet+}$ radical cations of the dumbbell so as to form (BIPY$^{\bullet+}$)$_2$ dimeric units. The reduction of the remaining four BIPY$^{2+}$ dication in both the dumbbell and the rings gives rise to the formation of trisradicals. Differential pulse voltammetry (DPV) experiments confirm the numbers of electrons involved in each step of the reduction process. Upon re-oxidation, these reduction processes are fully reversible, allowing the partially oxidized intermediates to be observed at −115 mV for 3R|4BP$^{16+}$ and at −135 mV for 3R|5BP$^{18+}$. These reduction processes are not observed in the corresponding oligopseudorotaxanes. These results suggest that the radical cationic forms of the oligorotaxanes are more difficult to oxidize than their oligopseudorotaxane progenitors, demonstrating their increased stabilities as a consequence of their mechanically interlocked structures, enforcing the BIPY$^{\bullet+}$ radical cations to come into close proximity.

Figures 11A, 11B:
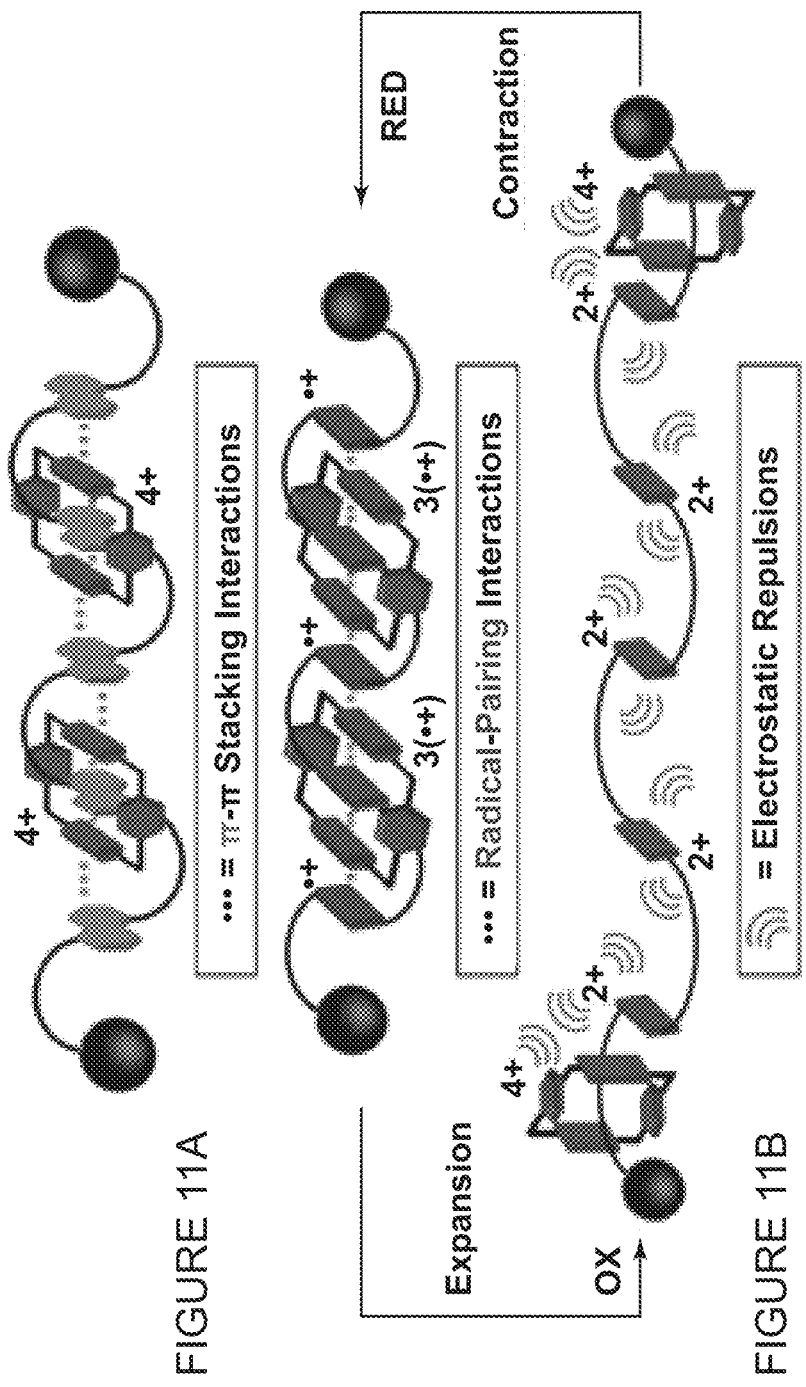
FIG. 11A shows an oligorotaxane with donor-acceptor interactions.
FIG. 11B shows an oligorotaxane where radical-pairing interactions stabilize the contracted form under reducing conditions and electrostatic repulsions favor the expanded form under oxidizing conditions.

In summary, we have reported a new class of oligorotaxanes, 3R|4BP•16PF$_6$ and 3R|5BP•18PF$_6$, which combine the advantages of both foldamers and mechanically interlocked molecules under reducing conditions. Composed of only positively charged components, it is only possible to access them by a template-directed approach that takes advantage of radical-pairing interactions, followed by a stoppering protocol employing Cu-free alkyne-azide cycloadditions. The formation of the key intermediates, oligopseudorotaxanes 4V$^{4(\bullet+)}$ ⊂ 2CBPQT$^{2(\bullet+)}$ and 5V$^{5(\bullet+)}$ ⊂ 2CBPQT$^{2(\bullet+)}$, are confirmed by both spectroscopic and electrochemical studies in solution. Computational studies reveal that these oligopseudorotaxanes preferentially form highly ordered secondary structures, wherein the CBPQT$^{2(\bullet+)}$ ring components play an important role in promoting all the BIPY$^{\bullet+}$ radical cations to stack in extended arrays, in order to maximize the stabilizing effect resulting from radical-pairing interactions. Comparison of the properties of the oligopseudorotaxanes with those of the oligorotaxanes shows that the secondary structures are further regulated in the oligorotaxanes since the components are obliged to remain in close proximity. More importantly, the redox-controlled actuation processes present (FIG. 11B) in these oligorotaxanes, which allow their secondary structures to be switched between folded and unfolded states, differentiate them from donor-acceptor,[20, 28] interactions-based systems (FIG. 11A). Moreover, these actuation processes lead to contractions and extensions of the oligorotaxanes, rendering them ideal prototypes of artificial molecular muscles. This research sheds light on the behavior of foldameric oligorotaxanes so that their structural and mechanical properties can be harnessed in devices.

Computational Studies of Oligopseudorotaxanes 4V$^{4(\bullet+)}$ ⊂ 2CBPQT$^{2(\bullet+)}$ and 5V$^{5(\bullet+)}$ ⊂ 2CBPQT$^{2(\bullet+)}$.

The folded co-conformations of the two oligopseudorotaxanes, 4V$^{4(\bullet+)}$ ⊂ 2CBPQT$^{2(\bullet+)}$ and 5V$^{5(\bullet+)}$ ⊂ 2CBPQT$^{2(\bullet+)}$, were investigated using the M06 of density functional theory. In addition to the general gradient approximation and kinetic energy functionals, M06 includes hybrid exact exchange to account for the localization needed to give good energies and has been optimized to account for van der Waals interactions important in supramolecular complexes. The superstructures were optimized at the M06L using the 6-31G* basis set while more accurate energies were obtained with single-point calculations at the M06 level using the 6-311++G** basis set. All calculations included solvation based on the Poisson-Boltzmann solvation model for MeCN (ε=37.5 and R$_0$=2.18 Å) implemented in Jaguar 7.7.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Materials and General Methods

Chemicals were purchased as reagent grade and used without further purification. Commercial grades of anhydrous MeCN and N,N-dimethylformamide (DMF) were used as solvents in all reactions. Benzyl viologen BnV•2PF$_6$ and compounds 1•6PF$_6$ and 3•8PF$_6$ were prepared[40, 42] according to literature procedures. Thin layer chromatography (TLC) was performed on silica gel 60F254 (E Merck). Column chromatography was carried out on silica gel 60F (Merck 9385, 0.040-0.063 mm). High performance liquid chromatography (HPLC) was performed on a preparative RP-HPLC instrument, using a C$_{18}$ column (Agilent, 10 μm packing, 30 mm×250 mm). The eluents employed were MeCN and H$_2$O, both mixed with 0.1% (v/v) trifluoroacetic acid (TFA). The detector was set to λ=254 nm. HPLC Analyses were performed on an analytical RP-HPLC instrument, using a C$_{18}$ column. For UV/Vis/Near Infrared (NIR) studies, all sample preparations were completed in an Argon-filled atmosphere. Samples were loaded into quartz 1 cm tubes and sealed with a clear ridged UV doming epoxy (IllumaBond 60-7160RCL) and used immediately after preparation. Nuclear magnetic resonance (NMR) spectra were recorded at 298 K on Bruker Avance 500 and 600 spectrometers, with working frequencies of 500 and 600 MHz for $^1$H, and 125 and 150 MHz for $^{13}$C nuclei, respectively. Chemical shifts are reported in ppm relative to the signals corresponding to the residual non-deuterated solvents.[3] EPR Spectra were recorded using a Bruker Elexsys E580-X EPR spectrometer, equipped with a variable Q dielectric resonator (ER-4118X-MD5-W1). Samples were prepared by reduction with cobaltocene and the solution was loaded into quartz 1.4 mm tubes and sealed with a clear ridged UV doming epoxy (IllumaBond 60-7160RCL). Samples were used immediately after preparation. Solution CW-EPR spectra were collected with a 0.4 G modulation amplitude 5.12 ms time constant and 20.48 ms conversion time. High-resolution mass spectra were measured on an Agilent 6210 Time-of-Flight (TOF) LC-MS, using an ESI source, coupled with Agilent 1100 HPLC stack, using direct infusion (0.6 mL min$^{-1}$). Measurements at X-band (9.5 GHz) were performed with a Bruker Elexsys E580, equipped with a variable Q dielectric resonator (ER-4118X-MD5-W1). Cyclic voltammetry experiments were performed on a Princeton Applied Research 263 A Multipurpose instrument interfaced to a PC, using a glassy carbon working electrode (0.071 cm$^2$, Cypress system). The electrode surface was polished routinely with an alumina/water slurry on a felt surface immediately before use. The counter electrode was a Pt coil and the reference electrode was an AgCl coated Ag wire. The concentrations of the samples were 1 mM in 100 mM electrolyte solutions of tetrabutylammonium hexafluorophosphate (TBAPF$_6$) in MeCN.

Scheme S1. One-Step Synthesis of 4BP•8PF$_6$ from 1•6PF$_6$

Figure 12:
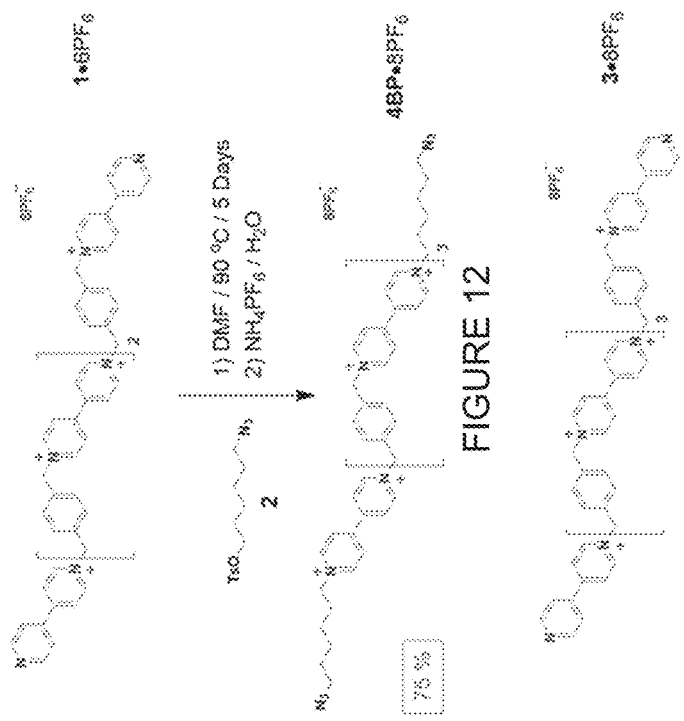
FIG. 12 shows a scheme for one-step synthesis of 4BP•8PF$_6$ from 1•6PF$_6$.

4BP•8PF$_6$: 1•6PF$_6$ (90 mg, 0.05 mmol) and 2 (148 mg, 0.5 mmol) were dissolved in DMF (10 mL) at room temperature. The reaction mixture was heated to 90° C. for 5 days and cooled down to room temperature, then Me$_2$CO was added to the solution. The resulting precipitate was filtered off, washed with Me$_2$CO, re-dissolved in H$_2$O, and re-precipitated by adding an excess of NH$_4$PF$_6$ (FIG. 12). The solid was filtered off and washed with H$_2$O, MeOH and finally Et$_2$O to afford 4BP•8PF$_6$ as a yellow solid (85 mg, 75%). $^1$H NMR (500 MHz, CD$_3$CN): δ=8.98 (d, J=6.9 Hz, 12H), 8.92 (d, J=6.9 Hz, 4H), 8.42 (d, J=5.1 Hz, 12H), 8.39 (d, J=5.1 Hz, 4H), 7.62 (s, 12H), 5.87 (s, 12H), 4.64 (t, J=7.6 Hz, 4H), 3.33 (t, J=6.8 Hz, 4H), 2.05 (p, J=7.4 Hz, 4H), 1.69-1.60 (m, 4H), 1.51-1.38 (m, 8H). $^{13}$C NMR (126 MHz, CD$_3$CN): δ=150.1, 145.3, 134.0, 130.0, 127.2, 127.2, 126.8, 63.5, 50.5, 30.4, 27.8, 25.3, 24.7. HRMS (ESI): m/z calcd for C$_{76}$H$_{80}$F$_{36}$N$_{14}$P$_6$ [M-2PF$_6$]$^{2+}$ 1029.7279. found 1029.7287.

Scheme S2. One-Step Synthesis of 5BP•10PF$_6$ from 3•8PF$_6$

Figure 13:
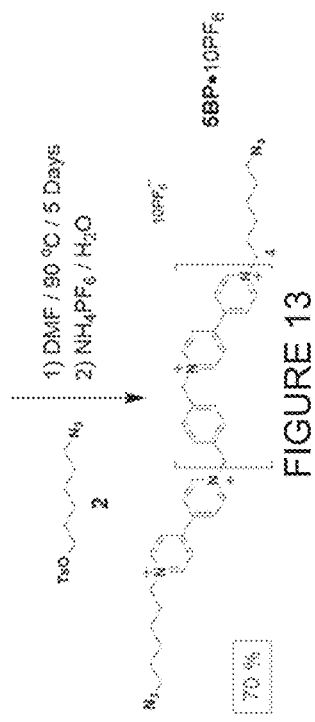
FIG. 13 shows a scheme for one-step synthesis of 5BP•10PF6 from 3•8PF6.

5BP•10PF$_6$: 3•8PF$_6$ (70 mg, 0.03 mmol) and 2 (89 mg, 0.3 mmol) were dissolved in DMF (10 mL) at room temperature. The reaction mixture was heated to 90° C. for 5 days and cooled down to room temperature, then Me$_2$CO was added to the solution. The resulting precipitate was filtered off, washed with Me$_2$CO, re-dissolved in H$_2$O, and re-precipitated by adding an excess of NH$_4$PF$_6$. (FIG. 13) The solid was filtered off and washed with H$_2$O, MeOH and finally Et$_2$O to afford 5BP•10PF$_6$ as a yellow solid (61 mg, 70%). $^1$H NMR (500 MHz, CD$_3$CN): δ=8.98 (d, J=6.9 Hz, 16H), 8.92 (d, J=6.9 Hz, 4H), 8.42 (d, J=5.1 Hz, 16H), 8.39 (d, J=5.1 Hz, 4H), 7.62 (s, 12H), 7.61 (s, 4H), 5.87 (s, 16H), 4.64 (t, J=7.6 Hz, 4H), 3.33 (t, J=6.8 Hz, 4H), 2.05 (p, J=7.4 Hz, 4H), 1.69-1.60 (m, 4H), 1.51-1.38 (m, 8H). $^{13}$C NMR (126 MHz, CD$_3$CN): δ=150.1, 145.3, 134.0, 130.0, 127.2, 127.2, 126.9, 63.5, 50.5, 30.4, 27.8, 25.3, 24.7. HRMS (ESI): m/z calcd for C$_{94}$H$_{96}$F$_{48}$N$_{16}$P$_8$ [M-2PF$_6$]$^{2+}$ 1304.7578. found 1304.7573.

Figure 14:
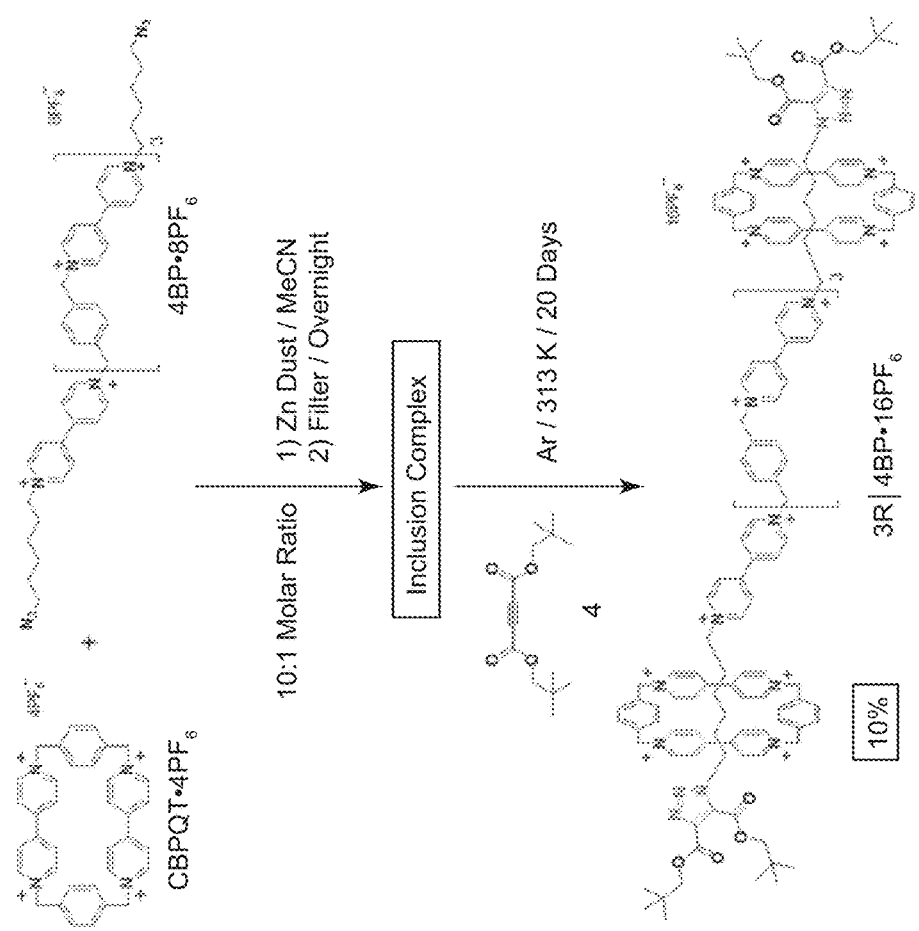
FIG. 14 shows a scheme for the synthesis of 3R|4BP•16PF6 from templated by radical-pairing interactions

Scheme S3. Synthesis of 3R|4BP•16PF$_6$ Templated by Radical-Pairing Interactions 3R|4BP•16PF$_6$: S3•8PF$_6$ (46 mg, 0.02 mmol) and CBPQT•4PF$_6$ (220 mg, 0.2 mmol) were dissolved in degassed MeCN (20 mL) in an Ar-filled glove box. An excess of Zn dust was added to this solution. After stirring for 30 mins, the colorless solution turned dark purple and the solid was filtered off. The purple filtrate was stirred overnight before compound 4 (51 mg, 0.2 mmol) was added. The reaction mixture was then heated to 40° C. and stirred under an Ar atmosphere for 20 days, during which time the reaction was monitored by RP-HPLC. (FIG. 14) The solvent was evaporated off, and the residue was purified by prep-HPLC (H$_2$O-MeCN, 0.1% TFA, 0-75% MeCN in 35 min). The fraction was combined and the solvent was evaporated off, and the solid was re-dissolved in H$_2$O, and precipitated by addition of an excess of NH$_4$PF$_6$. The solid was filtered off and washed with H$_2$O, MeOH and finally Et$_2$O to afford 3R|4BP•16PF$_6$ as a white solid (9 mg, 10%). $^1$H NMR (500 MHz, d$_6$-Me$_2$CO): δ=9.57 (d, J=7.2 Hz, 12H), 9.51 (d, J=6.2 Hz, 8H), 9.48 (d, J=6.2 Hz, 8H), 9.28 (d, J=6.2 Hz, 4H), 8.90 (d, J=6.4 Hz, 16H), 8.84 (d, J=6.4 Hz, 4H), 8.82-8.78 (m, 12H), 7.90-7.80 (m, 12H), 7.77 (s, 16H), 6.36-5.99 (m, 28H), 4.78 (t, J=8.4 Hz, 3H), 4.38 (s, 4H), 4.25 (s, 4H), 2.63 (t, J=8.4 Hz, 4H), 1.60 (br, 4H), 1.14 (s, 18H), 1.12 (s, 18H), 0.09 (br, 4H), 0.58 (br, 4H), 1.46 (br, 4H). $^{13}$C NMR (126 MHz, CD$_3$CN): δ=158.6, 150.7, 148.5, 146.2, 146.1, 145.6, 145.4, 136.3, 135.0, 130.6, 130.5, 130.4, 127.7, 127.6, 127.5, 76.7, 75.1, 64.9, 64.2, 48.9, 31.4, 31.3, 28.5, 28.3, 28.2, 25.9, 25.8, 25.7, 25.4. HRMS (ESI): m/z calcd for $C_{176}H_{188}F_{78}N_{22}O_8P_{13}$ [M-3PF$_6$]$^{3+}$ 1540.6775. found 1540.6770.

Figure 15:
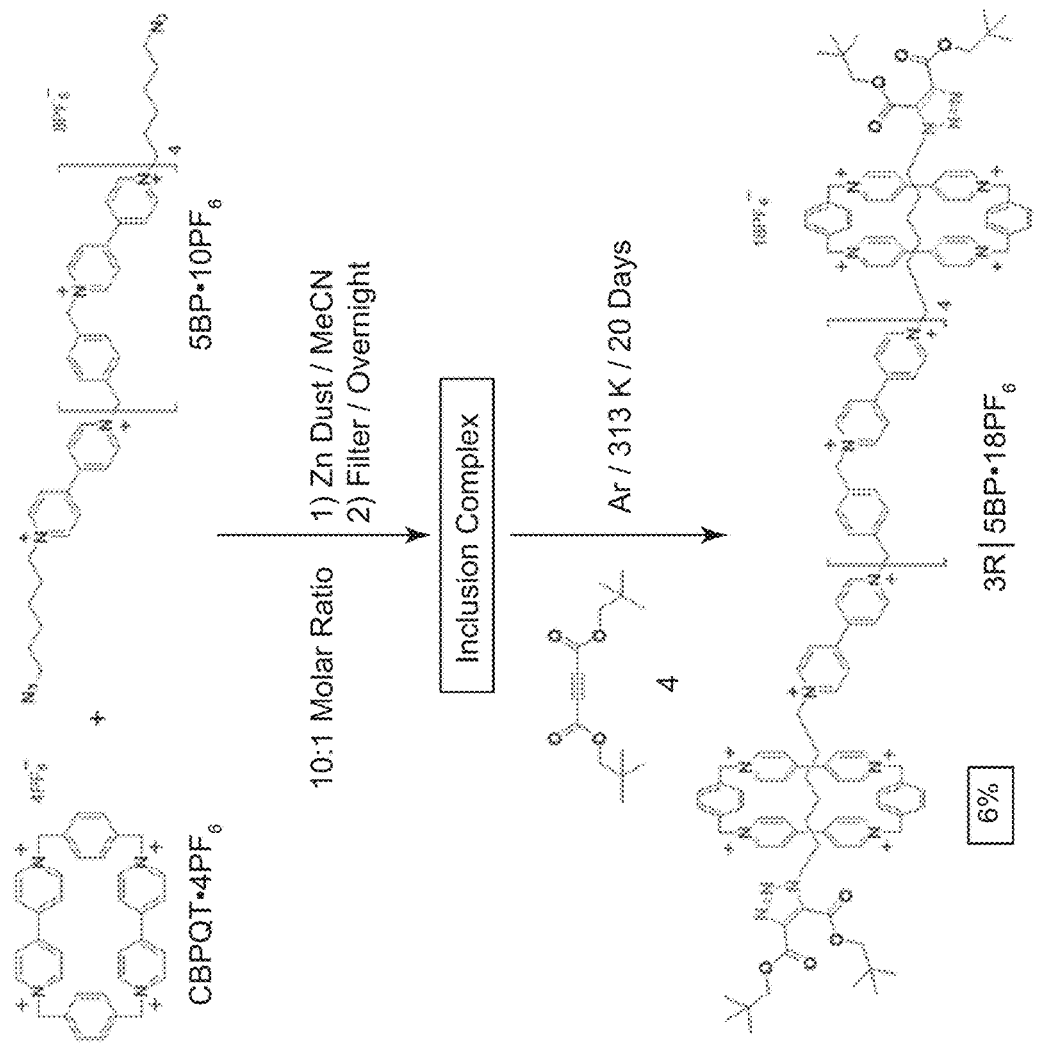
FIG. 15 shows a scheme for the synthesis of 3R|5BP•18PF$_6$ from templated by radical-pairing interactions FIG. 16 show a $^1$H NMR spectrum (500 MHz, CD$_3$COCD$_3$, 298K) of oligorotaxane 3R|4BP•16PF$_6$.

Scheme S4. Synthesis of 3R|5BP•18PF$_6$ Templated by Radical-Pairing Interactions 3R|5BP•18PF$_6$: 5BP•10PF$_6$ (58 mg, 0.02 mmol) and CBPQT•4PF$_6$ (220 mg, 0.2 mmol) were dissolved in degassed MeCN (20 mL) in an Ar-filled glove box. An excess of Zn dust was added to this solution. After stirring for 30 mins, the colorless solution turned dark purple and the solid was filtered off. The purple filtrate was stirred overnight before compound 4 (51 mg, 0.2 mmol) was added. The reaction mixture was then heated to 40° C. and stirred under an Ar atmosphere for 20 days, during which time the reaction was monitored by RP-HPLC (H$_2$O-MeCN, 0.1% TFA, 0-75% MeCN in 35 min). (FIG. 15) The solvent was evaporated off, and the residue was purified by prep-HPLC. The fraction was combined and the solvent was evaporated off, and the solid was re-dissolved in H$_2$O, and precipitated by addition of an excess of NH$_4$PF$_6$. The solid was filtered off and washed with H$_2$O, MeOH and finally Et$_2$O to afford 3R|5BP•18PF$_6$ as a yellow solid (6 mg, 6%). $^1$H NMR (500 MHz, d$_6$-Me$_2$CO): δ=9.57 (d, J=7.2 Hz, 12H), 9.51 (d, J=6.2 Hz, 8H), 9.48 (d, J=6.2 Hz, 8H), 9.28 (d, J=6.2 Hz, 4H), 8.90 (d, J=6.4 Hz, 16H), 8.84 (d, J=6.4 Hz, 4H), 8.82-8.78 (m, 12H), 7.90-7.80 (m, 12H), 7.77 (s, 16H), 6.36-5.99 (m, 28H), 4.78 (t, J=8.4 Hz, 3H), 4.38 (s, 4H), 4.25 (s, 4H), 2.63 (t, J=8.4 Hz, 4H), 1.60 (br, 4H), 1.14 (s, 18H), 1.12 (s, 18H), 0.05 (br, 4H), 0.61 (br, 4H), 1.51 (br, 4H). $^{13}$C NMR (126 MHz, CD$_3$CN): δ=158.6, 150.7, 148.5, 146.2, 146.1, 145.6, 145.4, 136.3, 135.0, 130.6, 130.5, 130.4, 127.7, 127.6, 127.5, 76.7, 75.1, 64.9, 64.2, 48.9, 31.4, 31.3, 28.5, 28.3, 28.2, 25.9, 25.8, 25.7, 25.4. HRMS (ESI): m/z calcd for $C_{194}H_{204}F_{90}N_{24}O_8P_{15}$ [M-3PF$_6$]$^{3+}$ 1724.7741. found 1724.7800.

$^1$H NMR Spectroscopic Analysis of Oligorotaxane 3R|4BP•16PF$_6$ and 3R|5BP•18PF$_6$.

Figure 16:
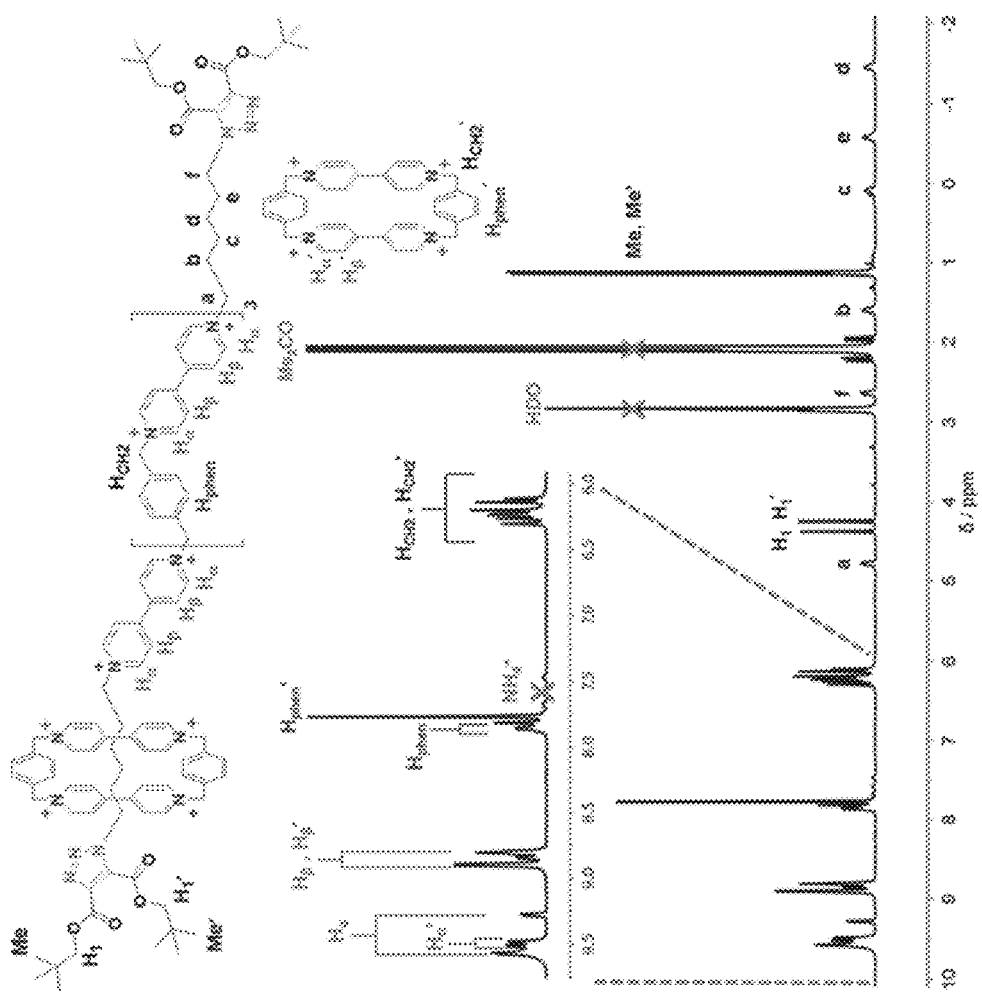

Compound 3R|4BP•16PF$_6$ has a simple $^1$H NMR spectrum (FIG. 16) on account of its high symmetry and only four BIPY$^{2+}$ subunits. In its oxidized state, the positive-charged CBPQT$^{4+}$ rings are positioned on the hexamethylene chains as a result of the Coulombic repulsions with the BIPY$^{2+}$ subunits of the thread, giving rise to the substantially lower resonating frequency (<0 ppm) of protons on the hexamethylene chains. In addition, the methyl groups of the stopper separate into two set of peaks, as a result of heterotopic nature of the triazole rings.

In the aromatic region of the spectrum, the signals for protons $H_\alpha$ and $H_\alpha'$ are well resolved. In particular, the resonances for $H_\alpha'$ on the CBPQT$^{4+}$ units appear as two set of peaks, presumably as a result of the free rotation of the BIPY$^{2+}$ units along the C—N bond being hindered by the hexamethylene chain. In contrast, the signals for protons $H_\beta$ and $H_\beta'$ on the dumbbell and the cyclophane CBPQT$^{4+}$, respectively, resonate at a similar frequencies, exhibiting overlapped peak signals. Protons on the hexamethylene chains were assigned unambiguously to resonances by identifying important through-bond couplings in the $^1$H-$^1$H gCOSY (FIGS. 17A-17B) such as $H_a \leftrightarrow H_b$, $H_b \leftrightarrow H_c$, $H_c \leftrightarrow H_d$, $H_d \leftrightarrow H_e$ and $H_e \leftrightarrow H_f$.

Figure 18:
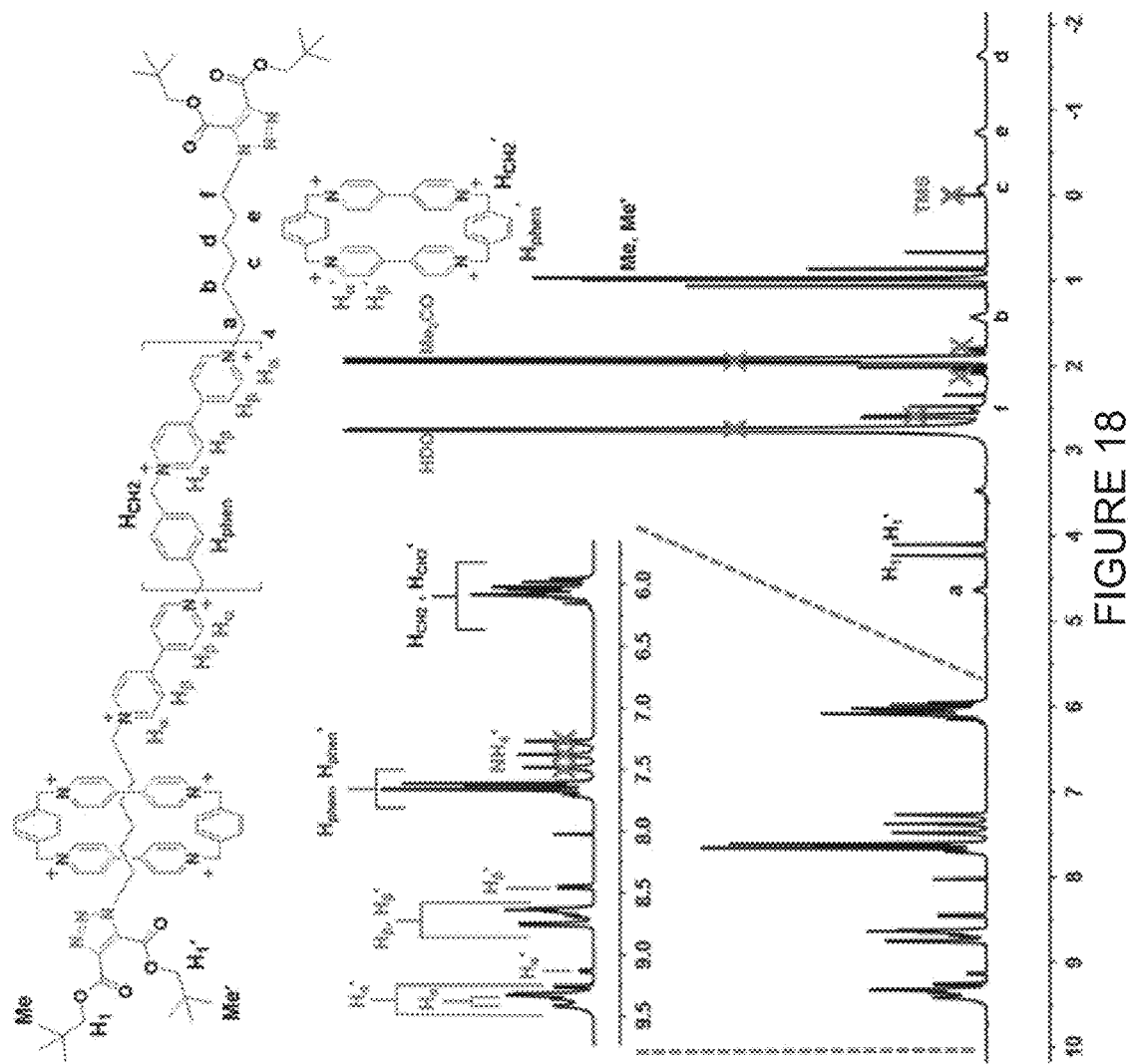
FIG. 18 shows a $^1$H NMR spectrum (500 MHz, CD$_3$COCD$_3$, 298K) of oligorotaxane 3R|5BP•18PF$_6$.

For compound 3R|5BP•18PF$_6$, the $^1$H NMR spectrum (FIG. 18) is more complicated because the dumbbell has one more BIPY$^{2+}$ subunit. Likewise, the protons of the hexamethylene chains can be assigned unambiguously to resonances by identifying important through-bond couplings in the $^1$H-$^1$H gCOSY (FIGS. 19A-19B) including $H_a \leftrightarrow H_b$, $H_b \leftrightarrow H_c$, $H_c \leftrightarrow H_d$, $H_d \leftrightarrow H_e$ and $H_e \leftrightarrow H_f$.

It is noteworthy that protons $H_c$, $H_d$ and $H_e$ of 3R|5BP•18PF$_6$ resonate slightly upfield compared with those in 3R|4BP•16PF$_6$, indicating that the CBPQT$^{4+}$ rings are pushed farther from the BIPY$^{2+}$ subunits on the dumbbell, presumably on account of the higher Coulombic repulsions as one more BIPY$^{2+}$ subunit is introduced into the rod portion of the dumbbell.

The protons of the aromatic region can be assigned by recording (FIG. 20) the $^1$H NMR spectrum at 233 K. The integral value and the splitting pattern indicate that the α and β protons of the BIPY$^{2+}$ in the CBPQT$^{4+}$ rings separate into four sets of peaks, presumably as a result of the rotation of the BIPY$^{2+}$ units of the CBPQT$^{4+}$ rings around the hexamethylene chain is 'frozen' under lower temperatures. The crossed peaks correspond to proton resonances of NH$_4^+$ from NH$_4$PF$_6$.

HPLC and HRMS Characterizations of Oligorotaxanes 3R|4BP•16PF$_6$ and 3R|5BP•18PF$_6$ The HPLC traces and the HRMS spectra of 3R|4BP•16PF$_6$ and 3R|5BP•18PF$_6$ are shown in FIGS. 21A-21B and FIGS. 22A-22D.

Job plots of 4V$^{4(•+)}$⊂2CBPQT$^{2(•+)}$ and 5V$^{5(•+)}$⊂2CBPQT$^{2(•+)}$

In order to verify the binding stoichiometry between CBPQT$^{2(•+)}$ and oligoviologen threads, we constructed a Job plot for 4V$^{4(•+)}$ and CBPQT$^{2(•+)}$ (FIGS. 23A-23B), as well as 5V$^{5(•+)}$ and CBPQT$^{2(•+)}$ (FIGS. 24A-24B) in MeCN.

The intensity of the trisradical complex absorption band at 1090 nm for 4V$^{4(•+)}$ and 1100 nm for 5V$^{5(•+)}$ was used for detecting the extent of binding as the molar ratio was varied. The Job plot is referenced to the concentration of CBPQT$^{2(•+)}$. The maximum intensity of the trisradical complex band occurred at χ=0.66, where x is the concentration of CBPQT$^{2(•+)}$ divided by the sum of concentration of CBPQT$^{2(•+)}$ and corresponding oligoviologen radical cationic species, indicating that both 4V$^{4(•+)}$ and 5V$^{5(•+)}$ bind two CBPQT$^{2(•+)}$ units in solution.

Figure 25A:
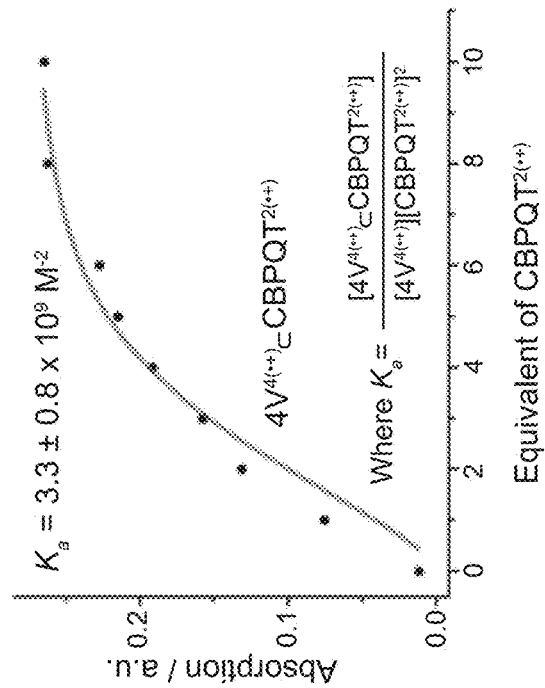
FIG. 25A shows a UV/Vis/NIR Absorption spectrophotometric titration experiment of 4V$^{4(•+)}$ by CBPQT$^{2(•+)}$ at 298 K. Solvent: MeCN; black: [4V$^{4(•+)}$]=10 μM; purple: c (CBPQT$^{2(•+)}$)/c (4V$^{4(•+)}$)=10.
Figure 25B:
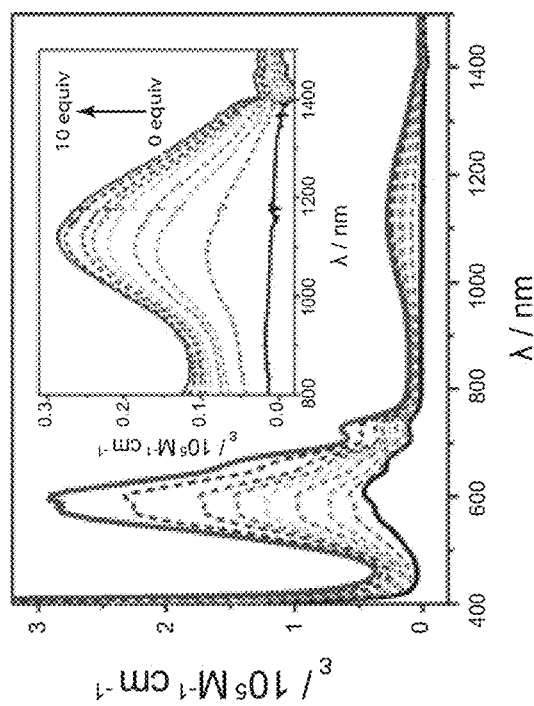
FIG. 25B shows a simulated curve for the determination of the binding constant between 4V$^{4(•+)}$ and CBPQT$^{2(•+)}$ from the data displayed in FIG. 25A.

UV/Vis/NIR Absorption Spectrophotometric Titration of 4V$^{4(•+)}$ and 5V$^{5(•+)}$ by CBPQT$^{2(•+)}$ FIGS. 25A-25B show a spectrophotometric titration of CBPQT$^{2(•+)}$ into a MeCN solution of 4V$^{4(•+)}$. This data was used to calculate a binding constant ($K_a$) of $3.3\pm0.8\times10^9$ M$^{-2}$ based on the 1:2 binding model.

Figure 26A:
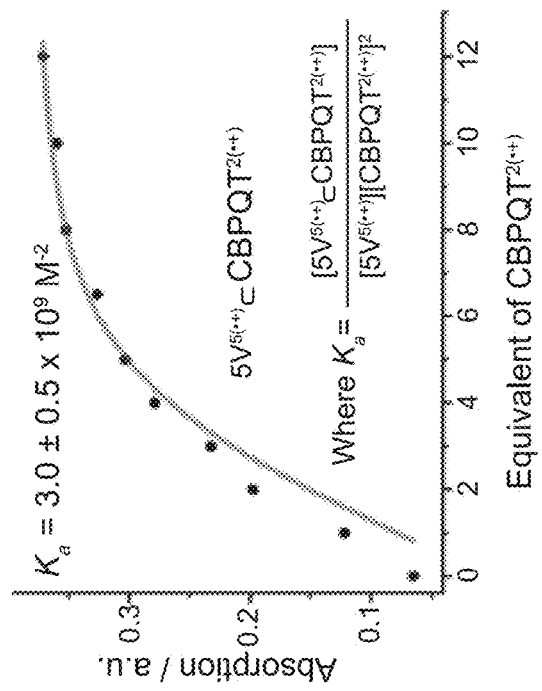
FIG. 26A shows a UV/Vis/NIR Absorption spectrophotometric titration experiment of 5V$^{5(•+)}$ by CBPQT$^{2(•+)}$ 298 K. Solvent: MeCN; black: [5V$^{5(•+)}$]=10 μM; purple: c (CBPQT$^{2(•+)}$)/c (5V$^{5(•+)}$)=12.
Figure 26B:
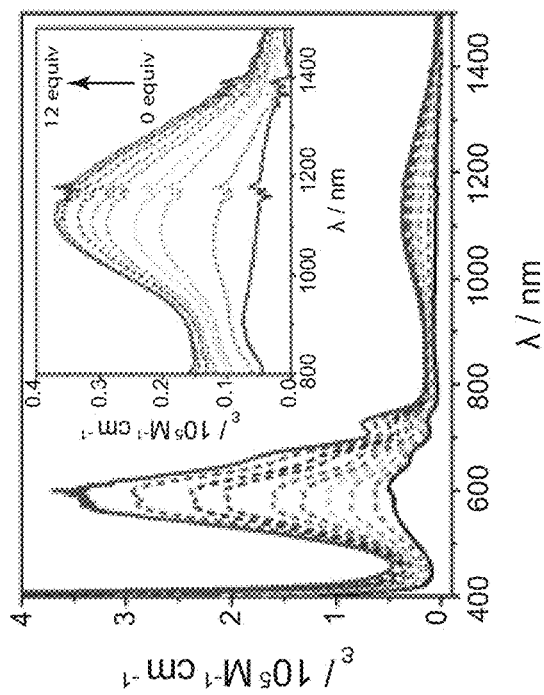
FIG. 26B shows a simulated curve for the determination of the binding constant between 5V$^{5(•+)}$ and CBPQT$^{2(•+)}$ from the data displayed in FIG. 25A.

FIGS. 26A-26B show a spectrophotometric titration of CBPQT$^{2(•+)}$ into a MeCN solution of 5V$^{5(•+)}$. This data was used to calculate a binding constant ($K_a$) of $3.0\pm0.5\times10^9$ M$^{-2}$ based on the 1:2 binding model as well. It is noteworthy that this $K_a$ value is comparable with that of 4V$^{4(•+)}$, indicating their similar abilities to bind CBPQT$^{2(•+)}$ in MeCN. As 5V$^{5(•+)}$ is one viologen unit longer than 4V$^{4(•+)}$, the binding process is less entropically favored. Therefore, the binding enthalpy between CBPQT$^{2(•+)}$ and 5V$^{5(•+)}$ is more negative to offset the additional entropy penalty. Moreover, this $K_a$ value is also close to the square of the binding constant[4] between CBPQT$^{2(•+)}$ and MV$^{•+}$ ($7.9\pm5.5\times10^4$ M$^{-1}$), demonstrating that the strength of binding between viologen units and the CBPQT$^{2(•+)}$ units is retained in the case of oligoviologens.

Variable-Temperature UV/Vis/NIR Spectroscopy of 3R|4BP•16PF$_6$

It is known that the radical-pairing interactions become weaker at higher temperature in solution. The structural information for the oligorotaxanes under reducing conditions, therefore, can be obtained by monitoring the change of the UV/Vis/NIR absorption intensities at different temperatures. Based on this knowledge, we selected 3R|4BP•16PF$_6$ as an example on which to perform a variable-temperature UV/Vis/NIR experiment.

Figure 27:
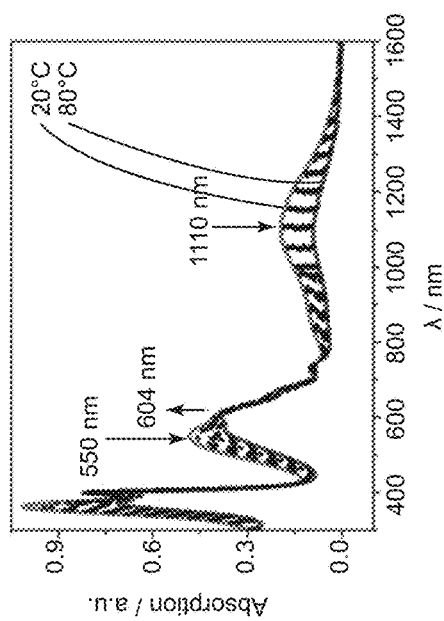
FIG. 27 shows a UV/Vis/NIR spectra of 3R|4BP•16PF$_6$ recorded at different temperatures ranging from 20° C. to 80° C. in MeCN at a concentration of 100 μM. The arrows in the figure denote the changing trend of the absorption intensities.

The spectra (FIG. 27) demonstrate that as the temperature of the solution increases, the absorption peaks centered at 550 and 1110 nm, which correspond to the formation of trisradical complex, decrease in their intensities. This observation suggests that the interactions between the CBPQT$^{2(•+)}$ ring and the BIPY$^{•+}$ units on the dumbbell are less favored at higher temperatures. As a result, the characteristic absorption band of unpaired BIPY$^{•+}$ units, i.e., the one at 604 nm, becomes more dominant at higher temperatures.
Cyclic voltammetry titration of $4V^{4(•+)} \subset 2CBPQT^{2(•+)}$ and $5V^{5(•+)} \subset 2CBPQT^{2(•+)}$ In order to shed further light on the interacting mechanism between $4V^{4(•+)}$ and CBPQT$^{2(•+)}$, a CV titration was performed.

Figure 28:
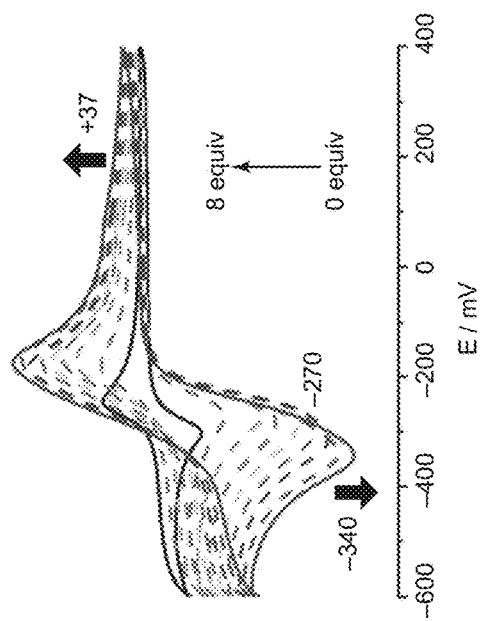
FIG. 28 shows a cyclic voltammogram titration of 4V$^{4(•+)}$⊂2CBPQT$^{2(•+)}$. A glassy carbon working electrode, a platinum counter electrode, and a Ag/AgCl reference electrode were used in the characterization of 0.1 mM MeCN solutions of the $4V^{8+}$ at 298 K with 0.1 M $TBAPF_6$ serving as the electrolyte. A scan rate of 200 mV s$^{-1}$ was used in all the analyses.

The result (FIG. 28) shows that upon increasing the amount of CBPQT$^{4+}$ from 1 equiv to 10 equiv, a reduction peak at −340 mV gradually emerges. It shifts toward the reduction potential of free CBPQT$^{4+}$, indicating the saturation of binding between $4V^{4(•+)}$ and CBPQT$^{2(•+)}$ when an excess of CBPQT$^{4+}$ is added to the solution. In addition, as the equiv of CBPQT$^{4+}$ increases in the solution, a peak shoulder with a potential of +37 mV can be observed, which is shifted significantly in the positive direction, indicating the existence of the radical dimer—namely, BIPY$^{•+}$ pimerization—a structure generated from the one-electron oxidation of the trisradical complex between $4V^{4(•+)}$ and CBPQT$^{2(•+)}$.

Figures 29, 30:
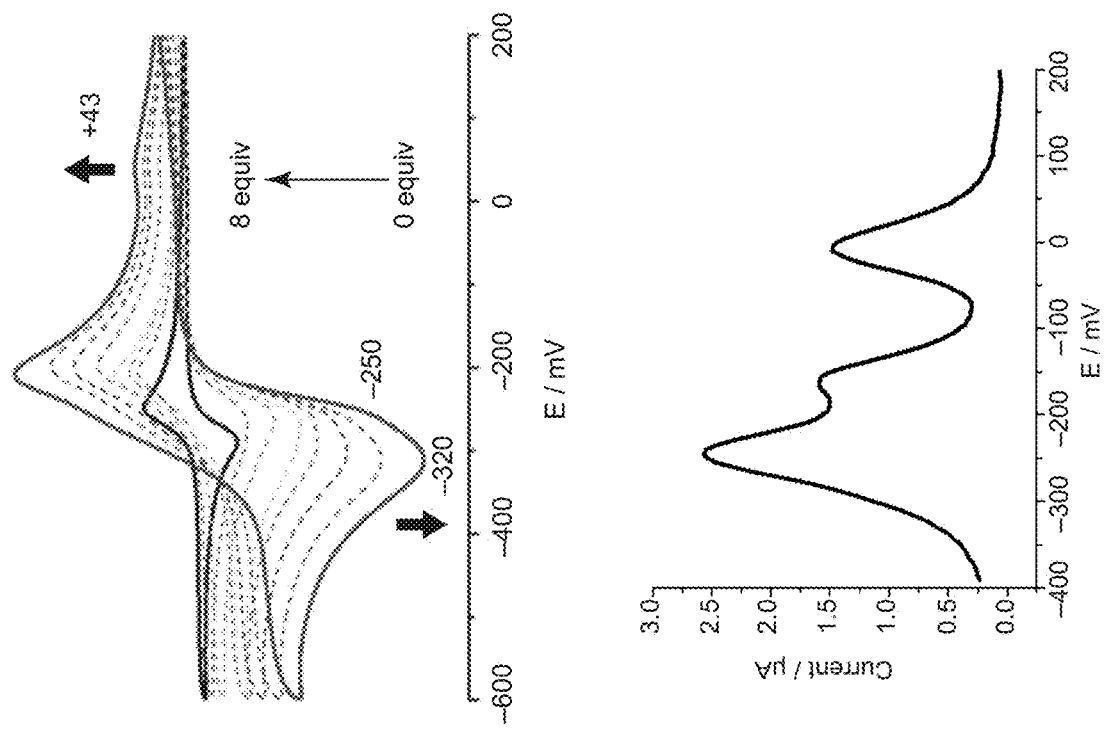
FIG. 29 shows a cyclic voltammogram titration of $5V^{5(\cdot+)} \subset 2CBPQT^{2(\cdot+)}$. A glassy carbon working electrode, a platinum counter electrode, and a Ag/AgCl reference electrode were used in the characterization of 0.1 mM MeCN solutions of the $5V^{10+}$ at 298 K with 0.1 M $TBAPF_6$ serving as the electrolyte. A scan rate of 200 mV s$^{-1}$ was used in all the analyses.
FIG. 30 shows a DPV profile of 3R|4BP•$16PF_6$. The ratio of the area under each peak (from right to left) is 1:1:2.

A CV titration experiment investigating (FIG. 29) the binding between $5V^{5(•+)} \subset 2CBPQT^{2(•+)}$ has also been carried out. Similarly, the saturation of binding was also confirmed by the observation of the reduction peak at −320 mV. In addition, the formation of the BIPY$^{•+}$ radical dimer can also be confirmed as a redox peak at +43 mV emerges upon oxidation. It is also noteworthy that this peak potential is shifted dramatically compared with that of the inclusion complex of $MV^{•+} \subset CBPQT^{2(•+)}$, presumably because the BIPY$^{•+}$ dimers between $4V^{4(•+)}$ and $5V^{5(•+)}$ with CBPQT$^{2(•+)}$ are more stable.

Differential Pulse Voltammetric Characterization of 3R|4BP•16PF$_6$

In order to gain a better understanding of the electron transfer processes during the formation of the radical states of these oligorotaxanes, as well as to find out how the mechanically interlocked structure affects the recognition between BIPY$^{•+}$ radicals, we selected 3R|4BP•16PF$_6$ as an example on which to perform a differential pulse voltammetry (DPV) experiment.

The DPV profile shows (FIG. 30) three bands during the reduction process, an observation which agrees with the results from CV experiments where the reduction of 3R|4BP$^{16+}$ to its radical state is complete after three steps. Comparison of the relative integrations associated with each band reveals a 1:1:2 ratio in relation to the numbers of electrons. Since a total number of eight electrons are involved during this reduction process, it can be concluded that the oligorotaxane 3R|4BP$^{16+}$ receives two, followed by two, followed by four, electrons during the course of the three steps.

Redox Stimuli-Induced Contraction and Expansion of 3R|4BP•16PF$_6$

Figure 31:
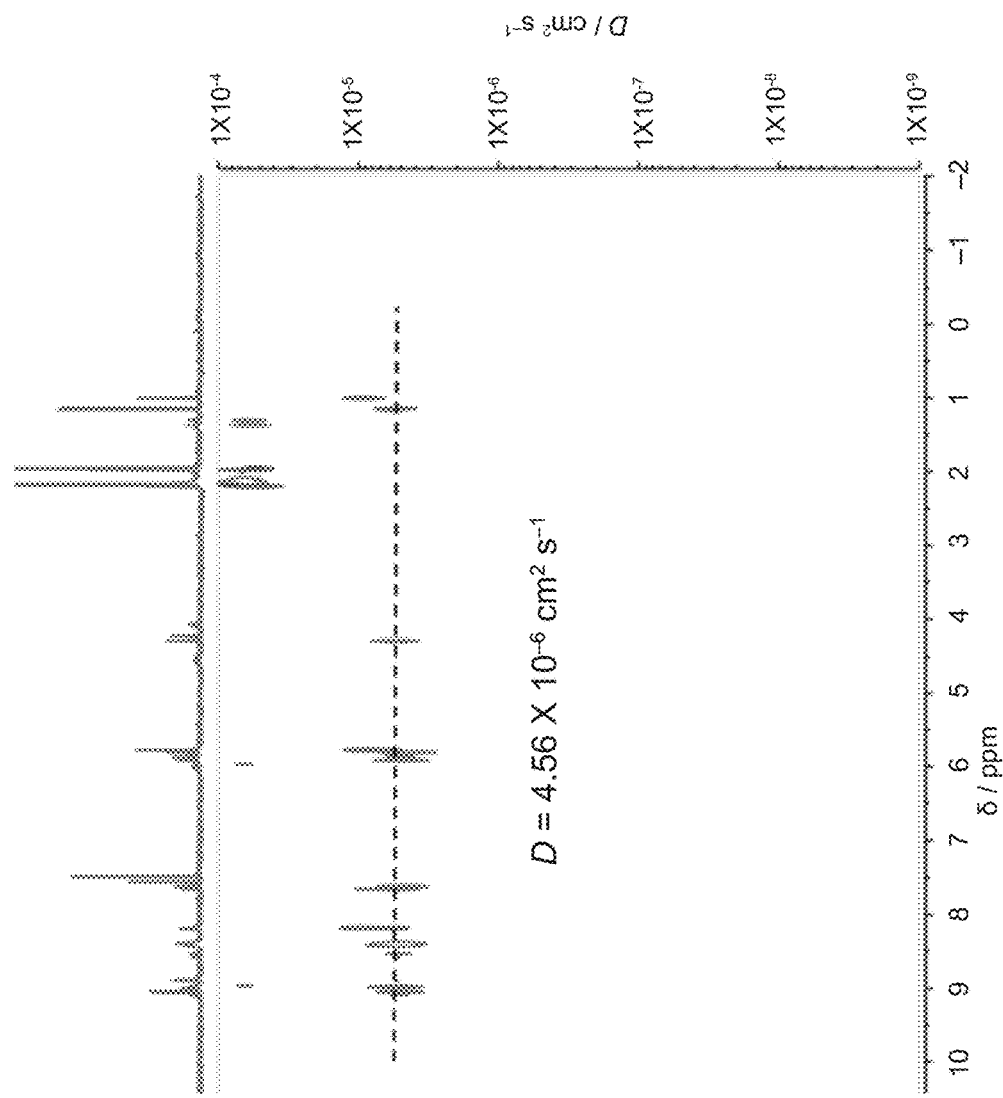
FIG. 31 shows a DOSY Spectrum (500 MHz, $CD_3CN$, 298 K) of 3R|4BP•$16PF_6$.
Figure 32A:
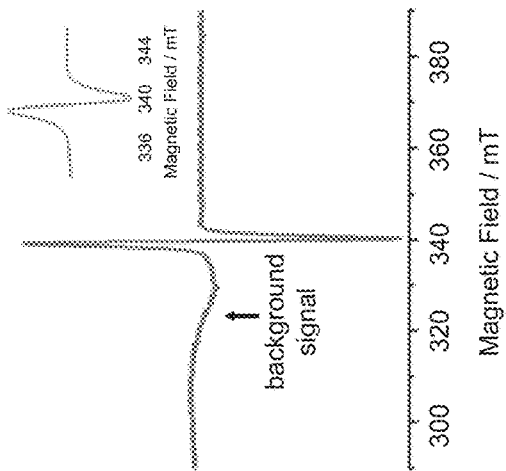
FIG. 32A shows a Cw-EPR spectra (X-Band) of the reference compound $BnV^{\cdot+}$ (top line) and the oligorotaxane $3R|4BP^{8(\cdot+)}$ (bottom line) in MeCN at RT. Modulation Amplitude: 0.1 G. Microwave frequency: 9.8240. Power: 0.395 mW.
Figure 32B:
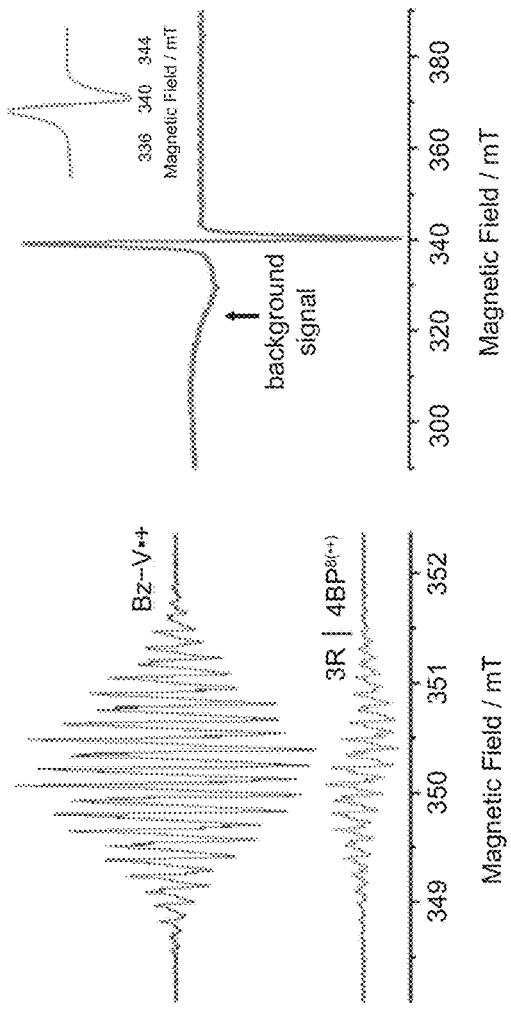
FIG. 32B shows a Cw-EPR spectra (X-Band) of 3R| $4BP^{8(\cdot+)}$ in frozen MeCN at 4.1 K. Concentration: 0.2 mM. Modulation Amplitude: 0.1 G. Microwave frequency: 9.8240. Power: 0.395 mW.

In order to gain an understanding of the changes in the lengths of the molecules during the redox-controlled switching processes of the oligorotaxanes, we selected 3R|4BP•16PF$_6$ as an example and performed diffusion ordered spectroscopy (DOSY) on its oxidized state (FIG. 31) and electron paramagnetic resonance (EPR) spectroscopy (FIGS. 32A-32B) on its reduced state.

The DOSY spectrum shows that the diffusion coefficient value (D) of 3R|4BP•16PF$_6$ in CD$_3$CN is $4.6 \times 10^{-6}$ cm$^2$ s$^{-1}$. Given the Einstein-Stokes equation D=kT/6πηr, the radius (r) of 3R|4BP•16PF$_6$ can be estimated as 1.4 nm. It should be noted, however, that this equation relates to spherical particles and so the DOSY can only give a rough estimation of molecular dimensions.

On the other hand, the dimension of the reduced state of 3R|4BP$^{16+}$, namely 3R|4BP$^{8(•+)}$, was investigated (FIGS. 32A-32B) by EPR spectroscopy. 3R|4BP$^{8(•+)}$ in MeCN (0.2 mM) can be generated by heterogeneous 8-electron reduction of 3R|4BP$^{16+}$ using freshly activated Zn dust in a N$_2$-filled glovebox. The radical cation benzyl viologen (BnV$^{•+}$) in MeCN (0.2 mM) was prepared in a similar fashion and used as a reference compound. A low sample concentration was employed in order to avoid any intermolecular interactions, and the samples were subjected to EPR measurements immediately after their preparation. The BnV$^{•+}$ solution at room temperature is blue-colored and shows (FIG. 32A) the typical cw X-Band EPR spectrum of a viologen radical cation, for which the g factor is 2.0031. The hyperfine structure can be rationalized on the basis of the electron spin coupling to two equivalent N atoms and 12H atoms, which can be divided further into two pairs of two methylene protons on the benzylic groups and two equivalent sets, each of four protons, on the bipyridinium core. In contrast, the EPR signal for the purple-colored 3R|4BP$^{8(•+)}$ under identical experimental conditions is fourfold weaker despite the fact that it contains eight viologen units per molecule. The weak intensity is indicative of a pronounced spin-pairing effect and is in line with the intramolecular diamagnetic π-dimerization. The detected weak EPR signal can be attributed to a small thermal population of paramagnetic co-conformations.

The cw-EPR spectrum of the octaradical 3R|4BP$^{8(•+)}$ even in frozen MeCN at 4.1 K shows (FIG. 32B) only one unresolved resonance. No clear evidence for high multiplicity (S>½) states can be observed, thus preventing the measurement of the zero-field splitting parameter D needed for estimation of the molecular diameter.

Figure 33A:
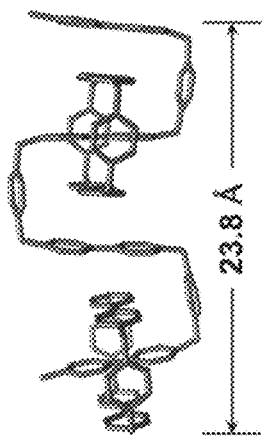
FIG. 33A shows the molecular length of $4V^{8+}$ measured on the simulated co-conformations.
Figure 33B:
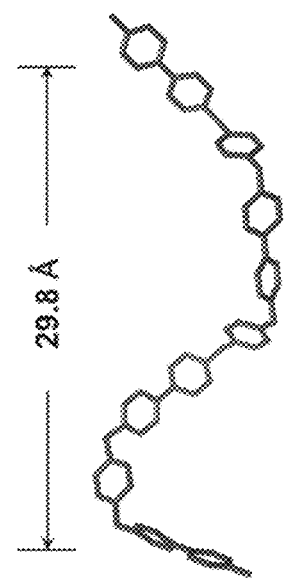
FIG. 33B shows the molecular length of $4V^{4(\cdot+)} \odot 2CBPQT^{2(\cdot+)}$ measured on the simulated co-conformations.

The change in the length of the oligorotaxane 3R|4BP$^{16+}$ on reduction to 3R|4BP$^{8(•+)}$ is supported by computational analysis. Since 3R|4BP$^{16+}$ is too large to be simulated by DFT calculations, we sought an approximation by comparing the "central regions" of 3R|4BP$^{16+}$ and 3R|4BP$^{8(•+)}$. We measured the centroid-centroid distance between the two terminal BIPY$^{2+}$ units in the simulated conformation (FIG. 33A) of $4V^{8+}$ and the centroid-centroid distance between the two terminal BIPY$^{•+}$ units—one on the $4V^{4(•+)}$ component and the other on the distant CBPQT$^{2(•+)}$ ring—in the co-conformation (FIG. 33B) of the oligopseudorotaxane $4V^{4(•+)} \subset 2CBPQT^{2(•+)}$. It turns out that, upon reduction, the molecular length contracts by 6 Å from 29.8 to 23.8 Å. This result confirms our conclusion that the oligorotaxanes experience expansion-contraction movements during the redox-stimulated processes.

Computational Details of Oligoviologens Folding with CBPQT$^{2(•+)}$

The geometries were optimized at M06L/6-31G* level in the presence of the Poisson-Boltzmann solvation model for acetonitrile (ε=37.5 and R$_0$=2.18 Å). Different C—C bond torsions are chosen as the initial structures to give different number of BIPY$^{2(•+)}$ pairs. The single point energies were refined at M06/6-311++G** level. The optimized structures reported in the FIGS. 6A-6D of the main text are provided below, with the calculated energies at each level. Units are in Hartree.

| M06L/6-31G* in acetonitrile (A) | M06L/6-31G* in gas phase (B) | M06/6-311++G** in gas phase (C) | Total energy (C + A − B) |
|---|---|---|---|
| Co-conformation 3a | | | |
| −6208.69096 | −6206.86399 | −6204.35455 | −6206.18151 |
| Co-conformation 3b | | | |
| −6208.69356 | −6206.99997 | −6204.48428 | −6206.17787 |
| Co-conformation 3c | | | |
| −6208.68304 | −6206.95888 | −6204.446 | −6206.17016 |
| Co-conformation 3d | | | |
| −6208.68477 | −6206.90408 | −6204.38941 | −6206.17010 |
| Co-conformation 3e | | | |
| −7013.50973 | −7011.31315 | −7008.47273 | −7010.66930 |
| Co-conformation 3f | | | |
| −7013.48893 | −7011.40759 | −7008.57209 | −7010.65344 |
| Co-conformation 3g | | | |
| −7013.48517 | −7011.39524 | −7008.55690 | −7010.64683 |
| Co-conformation 3h | | | |
| −7013.47898 | −7011.56174 | −7008.7199 | −7010.63714 |

REFERENCES

1. Aida, T. et al. Functional supramolecular polymers. Science 2012, 335, 813-817.
2. Evans, N. H.; Beer, P. D. Advances in anion supramolecular chemistry: from recognition to chemical applications. Angew. Chem. Int. Ed. 2014, 53, 11716-11754.
3. Schneider, H. J. Dispersive interactions in solution complexes. Acc. Chem. Res. 2015, 48, 1815-1822.
4. Mattia, E.; Otto, S. Supramolecular systems chemistry. Nat. Nanotechnol. 2015, 10, 111-119.
5. Hill, D. J. et al. A field guide to foldamers. Chem. Rev. 2001, 101, 3893-4011.
6. Sessler, J. L.; Jayawickramarajah, J. Functionalized basepairs: versatile scaffolds for self-assembly. Chem. Commun. 2005, 1939-1949.
7. Guichard, G.; Huc, I. Synthetic foldamers. Chem. Commun. 2011, 47, 5933-5941.
8. Zhang, D. W. et al. Aromatic amide and hydrazide foldamer-based responsive host-guest systems. Acc. Chem. Res. 2014, 47, 1961-1970.
9. Kay, E. R. et al. Synthetic molecular motors and mechanical machines. Angew. Chem. Int. Ed. 2007, 46, 72-191.
10. Bruns, C. J.; Stoddart, J. F. The mechanical bond: a work of art. Top. Curr. Chem. 2012, 323, 19-72.
11. Coskun, A. et al. Great expectations: can artificial molecular machines deliver on their promise? Chem. Soc. Rev. 2012, 41, 19-30.
12. Luo, Z. et al. Engineering a hollow nanocontainer platform with multifunctional molecular machines for tumor-targeted therapy in vitro and in vivo. ACS Nano 2013, 7, 10271-10284.
13. Barat, R. et al. A mechanically interlocked molecular system programmed for the delivery of an anticancer drug. Chem. Sci. 2015, 6, 2608-2613.
14. Flood, A. H. et al. Whence molecular electronics? Science 2004, 306, 2055-2056.
15. Coskun, A. et al. High hopes: can molecular electronics realise its potential? Chem. Soc. Rev. 2012, 41, 4827-4859.
16. Venturi, M.; Credi, A. Electroactive [2]catenanes. Electrochim. Acta 2014, 140, 467-475.
17. Gotz, G. et al. pi-Conjugated [2]catenanes based on oligothiophenes and phenanthrolines: efficient synthesis and electronic properties. Chem. Eur. J. 2015, 21, 7193-7210.
18. Gan, Q. A. et al. Helix-rod host-guest complexes with shuttling rates much faster than disassembly. Science 2011, 331, 1172-1175.
19. Zhang, K. D. et al. Foldamer-tuned switching kinetics and metastability of [2]rotaxanes. Angew. Chem. Int. Ed. 2011, 50, 9866-9870.
20. Zhu, Z. et al. Synthesis and solution-state dynamics of donor-acceptor oligorotaxane foldamers. Chem. Sci. 2013, 4, 1470-1483.
21. Wozny, M. et al. An electrochemically switchable foldamera surprising feature of a rotaxane with equivalent stations. Chem. Sci. 2014, 5, 2836-2842.
22. Pinson, M. B. et al. Mobile rings on a polyrotaxane lead to a yield force. Macromolecules 2013, 46, 4191-4197.
23. Katsuno, C. et al. Pressure-responsive polymer membranes of slide-ring gels with movable cross-links. Adv. Mater. 2013, 25, 4636-4640.
24. Van Quaethem, A. et al. Probing the mobility of catenane rings in single molecules. Chem. Sci. 2014, 5, 1449-1452.
25. Bin Imran, A. et al. Extremely stretchable thermosensitive hydrogels by introducing slide-ring polyrotaxane cross-linkers and ionic groups into the polymer network. Nat. Commun. 2014, 5.
26. Inutsuka, M. et al. Highly dielectric and flexible polyrotaxane elastomer by introduction of cyano groups. Polymer 2015, 59, 10-15.
27. Du, G. Y. et al. Muscle-like supramolecular polymers: integrated motion from thousands of molecular machines. Angew. Chem. Int. Ed. 2012, 51, 12504-12508.
28. Bruns, C. J.; Stoddart, J. F. Mechanically interlaced and interlocked donor-acceptor foldamers. Adv. Polym. Sci. 2013, 261, 271-294.
29. Trabolsi, A. et al. Radically enhanced molecular recognition. Nat. Chem. 2010, 2, 42-49.
30. Fahrenbach, A. C. et al. Radically enhanced molecular switches. J. Am. Chem. Soc. 2012, 134, 16275-16288.
31. Barnes, J. C. et al. A Radically configurable six-state compound. Science 2013, 339, 429-433.
32. Li, H. et al. Mechanical bond-induced radical stabilization. J. Am. Chem. Soc. 2013, 135, 456-467.
33. Cheng, C. Y. et al. An artificial molecular pump. Nat. Nanotechnol. 2015, 10, 547-553.
34. Feringa, B. L. Molecular machines springing into action. Nat. Chem. 2010, 2, 429-430.
35. Dawson, R. E. et al. The foundation of a light driven molecular muscle based on stilbene and alpha-cyclodextrin. Chem. Commun. 2008, 34, 3980-3982.
36. Balzani, V. et al. Light powered molecular machines. Chem. Soc. Rev. 2009, 38, 1542-1550.
37. Takashima, Y. et al. Expansion-contraction of photoresponsive artificial muscle regulated by host-guest interactions. Nat. Commun. 2012, 3, 1270-1277.
38. Bruns, C. J.; Stoddart, J. F. Rotaxane-based molecular muscles. Acc. Chem. Res. 2014, 47, 2186-2199.

39. Durot, S. et al. Transition-metal-complexed catenanes and rotaxanes: from dynamic systems to functional molecular machines. Top. Curr. Chem. 2014, 354, 35-70.
40. Wang, Y. et al. Folding of oligoviologens induced by radical-radical interactions. J. Am. Chem. Soc. 2015, 137, 876-885.
41. Fahrenbach, A. C. et al. Solution-phase mechanistic study and solid-state structure of a tris(bipyridinium radical cation) inclusion complex. J. Am. Chem. Soc. 2012, 134, 3061-3072.
42. Sharrett, Z. et al. The effect of boronic acid acidity on performance of viologen-based boronic acids in a two-component optical glucose-sensing system. *Tetrahedron Lett* 2007, 48, 5125-5129,
43. Fulmer, G. R. et al. NMR chemical shifts of trace impurities: common laboratory solvents, organics, and gases in deuterated solvents relevant to the organometallic chemist. *Organometallics* 2010, 29, 2176-2179.

All references, including publications, patent applications, and patents, cited herein are hereby incorporated by reference to the same extent as if each reference were individually and specifically indicated to be incorporated by reference and were set forth in its entirety herein.

We claim:

1. An nanoaccuator comprising a rotaxane,
   wherein the rotaxane comprises a threading component and at least two macrocylic components;
   wherein the threading component comprises a oligoviologen;
   wherein the threading component is threaded through each of the macrocylic components and
   wherein the at least two macrocylic components are CBPQT macrocylic components.

2. The nanoaccuator of claim 1, wherein the threading component further comprises a first linking subunit, L, and/or a second linking subunit, L'.

3. The nanoaccuator of claim 1,
   wherein the threading component further comprises a first stopper, S, and/or a second stopper, S'.

4. The nanoaccuator of claim 2,
   wherein the threading component further comprises a first stopper, S, and/or a second stopper, S' and
   wherein the L links a first end of the oligoviologen to S and the L' links a second end of the oligoviologen to the S'.

5. The nanoaccuator of claim 1, wherein the oligoviologen comprises n+1 viologen subunits, V, and wherein n is an integer.

6. The nanoaccuator of claim 5, wherein V is a BIPY subunits.

7. The nanoaccuator of claim 1, wherein the oligoviolgen further comprises n bridging subunits, B, linking the viologen subunits.

8. The nanoaccuator of claim 7, wherein B is a paraxylene subunit.

9. The nanoaccuator of claim 5, wherein n is 3 or 4.

10. The nanoaccuator of claim 2, wherein the first linking subunit, L, the second linking subunit, L', or both the first linking subunit and the second linking subunit comprise an alkyl subunit.

11. The nanoaccuator of claim 2, wherein L is a polyethylene oxide, L' is a polyethylene oxide, or both L and L' are polyethylene oxides.

12. The nanoaccuator of claim 3,
    wherein S is a triazole stopper moiety having a formula of R—$C_2N_3$—R', S' is a triazole stopper moiety having a formula of R—$C_2N_3$—R', or both of S and S' are triazole stopper moieties having the formula R—$C_2N_3$—R', and
    wherein R and R' are bulky moieties capable of preventing dethreading of the macrocyclic components.

13. The nanoaccuator of claim 1, wherein the rotaxane is complexed with an anion.

14. The nanoaccuator of claim 13, wherein the anion is $PF_6^-$ or $CF_3C(=O)O^-$.

15. The nanoaccuator of claim 1, wherein the reducing the rotaxane contracts the nanoreactor and/or oxidizing the rotaxane extends the nanoactuator.

16. The nanoaccuator of claim 1, wherein the nanoactuator is capable of reversible contraction and extension.

17. A nanoaccuator comprising a rotaxane,
    wherein the rotaxane comprises a threading component;
    wherein the threading component comprising a linear subchain having a formula L-V-[B-V]$_n$-L', and at least two macrocycle components;
    wherein each of the at least two macrocycle components are threaded onto the threading component;
    wherein V is a viologen subunit;
    wherein B is a bridging subunit;
    wherein L and L' are linking subunits;
    wherein n is an integer, and
    wherein the at least two macrocylic components are CBPQT macrocylic components.

18. The nanoaccuator of claim 17,
    wherein the threading component further comprises a first stopper subunit, S, and a second stopper subunit, S', and
    wherein the threading component has a formula of S-L-V-[B-V]$_n$-L'-S'.

19. A method of accuating a nanoactuator, the method comprising oxidating or reducing a nanoreactor as in claim 1,
    wherein oxidizing the nanoactuator extends the nanoactuator and reducing the nanoactuator contracts the nanoactuator.

* * * * *